United States Patent
Spees

(10) Patent No.: US 9,707,271 B2
(45) Date of Patent: Jul. 18, 2017

(54) METHODS FOR ENHANCING CARDIAC FUNCTION WITH THE COMBINATION OF CTGF AND INSULIN OR IGF-1

(71) Applicant: University of Vermont and State Agriculture College, Burlington, VT (US)

(72) Inventor: Jeffrey Spees, Colchester, VT (US)

(73) Assignee: University of Vermont and State Agriculture College, Burlington, VT (US)

( * ) Notice: Subject to any disclaimer, the term of this patent is extended or adjusted under 35 U.S.C. 154(b) by 0 days.

(21) Appl. No.: 14/771,747

(22) PCT Filed: Mar. 7, 2014

(86) PCT No.: PCT/US2014/022094
§ 371 (c)(1),
(2) Date: Aug. 31, 2015

(87) PCT Pub. No.: WO2014/138682
PCT Pub. Date: Sep. 12, 2014

(65) Prior Publication Data
US 2016/0008428 A1 Jan. 14, 2016

Related U.S. Application Data

(60) Provisional application No. 61/775,285, filed on Mar. 8, 2013.

(51) Int. Cl.
| | | |
|---|---|---|
| A61P 9/04 | (2006.01) | |
| A61P 9/10 | (2006.01) | |
| A61K 35/34 | (2015.01) | |
| A61K 38/18 | (2006.01) | |
| A61K 38/28 | (2006.01) | |
| A61K 38/30 | (2006.01) | |
| C07K 14/475 | (2006.01) | |
| C07K 14/62 | (2006.01) | |
| C07K 14/65 | (2006.01) | |

(52) U.S. Cl.
CPC .............. *A61K 38/18* (2013.01); *A61K 35/34* (2013.01); *A61K 38/28* (2013.01); *A61K 38/30* (2013.01); *C07K 14/475* (2013.01); *C07K 14/62* (2013.01); *C07K 14/65* (2013.01)

(58) Field of Classification Search
None
See application file for complete search history.

(56) References Cited

U.S. PATENT DOCUMENTS

2011/0275563 A1  11/2011  Attramadal et al.

FOREIGN PATENT DOCUMENTS

| WO | 2007/066823 | 6/2007 | |
|---|---|---|---|
| WO | WO 2010138180 A2 * | 12/2010 | ............. A61K 35/34 |
| WO | 2011/057249 A2 | 5/2011 | |

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Takeda et al., "Cellular interplay between cardiomycytes and nonmyocytes in cardiac remodeling," International Journal of Inflammation, 2011, vol. 2011, pp. 1-13, Especially p. 5, col. 1, para 1-2; p. 5, col. 2, para 1.
Kofidis et al., "Insulin-Like Growth Factor promotes engraftment, differentiation, and functional impreovement after transfer of embryonic stem cells for myocardial restoration," Stem Cells. Dec. 2004, vol. 22, No. 7, pp. 1239-1245. Especially Abstract; p. 1243, col. 1, para 1-4; p. 1423, col. 2., para 1; p. 1244, col. 1, para 1; p. 1240; col. 2, para 2; p. 1240, col. 2, para 4; p. 1242, col. 1, para 2; p. 1242, col., 2, para 1-2; p. 1240, col. 1, para 2.
Liu et al., "Early stem cell engraftment predicts late cardiac functional recovery: Pre-clinical insights from molecular imaging," Circ. Cardiovasc. Imaging, Jul. 1, 2012, vol. 5, No. 4, pp. 481-490, especially p. 5, para 2, para 4; p. 3, para 7; p. 3, para 2.
Notification of Transmittal of the International Search Report and the Written Opinion of the International Searching Authority of corresponding PCT/US2014/022094, mailed Jun. 18, 2014, 11 pages.
Ahmed, M Shakil et al., "Mechanisms of novel cardioprotective functions of CCN2/CTGF in myocardial ischemia-reperfusion injury", American Journal of Physiology—Heart and Circulatory Physiology, vol. 200, No. 4, pp. H1291-H1302, Apr. 2011.
Ellison, Georgina M. et al., "Endogenous Cardiac Stem Cell Activation by Insulin-Like Growth Factor-1/Hepatocyte Growth Factor Intracoronary Injection Fosters Survival and Regeneration of the Infarcted Pig Heart", Journal of the 4merican College of Cardiology, Elsevier, New York, NY, US, vol. 58, No. 9, pp. 977-986, May 24, 2011.
Grotendorst, Gary et al., "Individual domains of connective tissue growth factor regulate fibroblast proliferation and myofibroblast differentiation", FASEB Journal: Official Publication of the Federation of American Societies for Experimental Biology May 2005, vol. 19, No. 7, pp. 729-738, May 7, 2005.
Liu, B.C., et al, "Role of connective tissue growth factor (CTGF) module 4 in a regulating epithelial mesenchymal transition (EMT) in HK-2 cells", Clinica Chimica Acta, Lesevier BV, Amsterdam, NL, vol. 373, No. 1-2, pp. 144-150, Nov. 1, 2006.

(Continued)

*Primary Examiner* — Zachary Howard
(74) *Attorney, Agent, or Firm* — Melissa Hunter-Ensor; Elbert Chiang; Greenberg Traurig, LLP

(57) ABSTRACT

The invention features compositions featuring (a) one or more of connective tissue growth factor (CTGF) and human C-terminal CTGF peptide; and (b) one or more of insulin and IGF-1; and methods of using such compositions to reduce cardiac tissue damage associated with an ischemic event or to enhance engraftment of a cell in a cardiac tissue.

8 Claims, 20 Drawing Sheets

(56) References Cited

OTHER PUBLICATIONS

Martinov, Vladimir N et al., "CCN2:CTGF as a Novel Stimulator of Proliferation and Survivial of Cardiac Progenitor Cells/Stem Cells", Circulation, Lippincott Williams& Wilkins, US, vol. 122, No. 21, Suppl, pp. A19874, Nov. 1, 2010.
Extended European Search Report issued in European Patent Application No. 14760147.0 mailed Jul. 29, 2016.

* cited by examiner

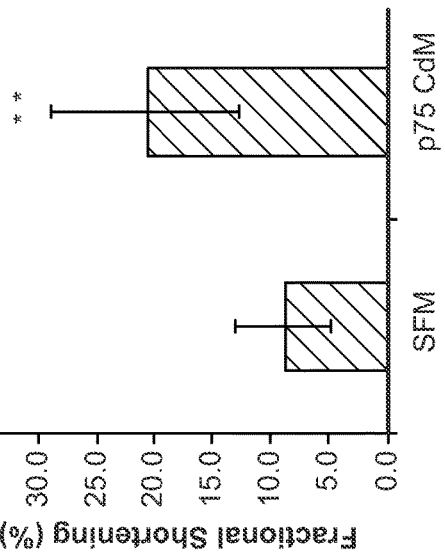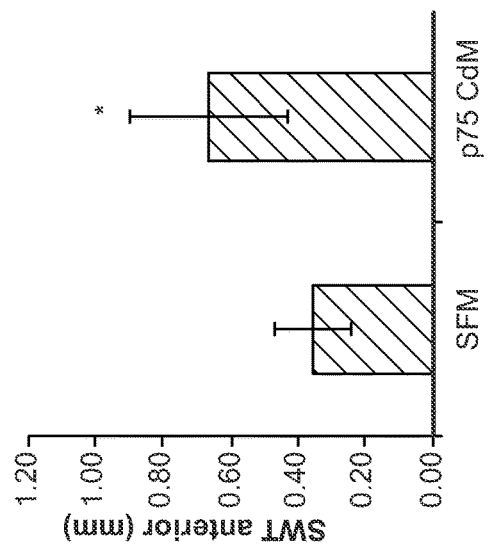
FIG. 8B
FIG. 8D
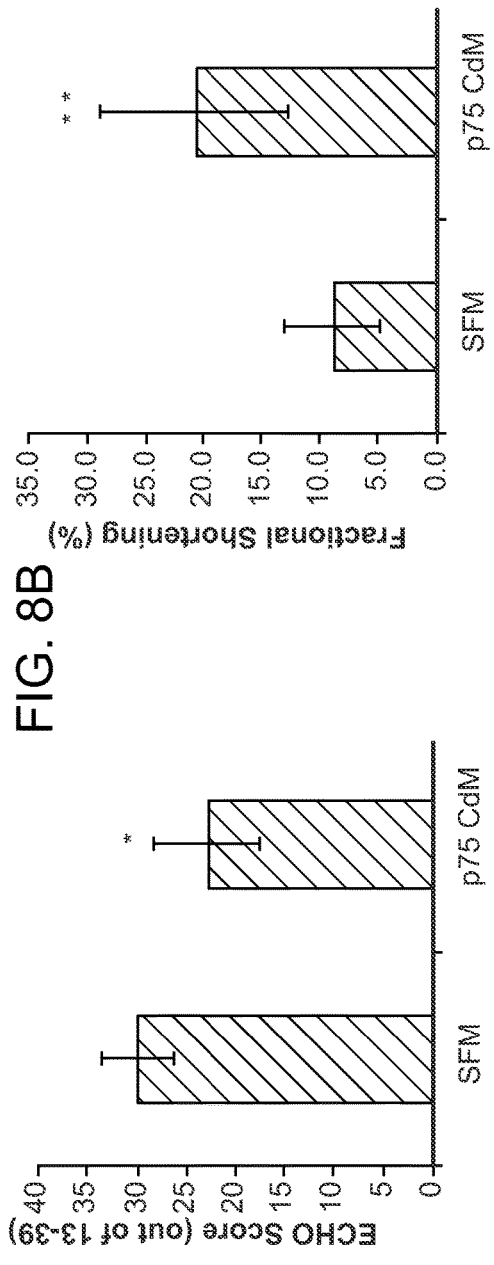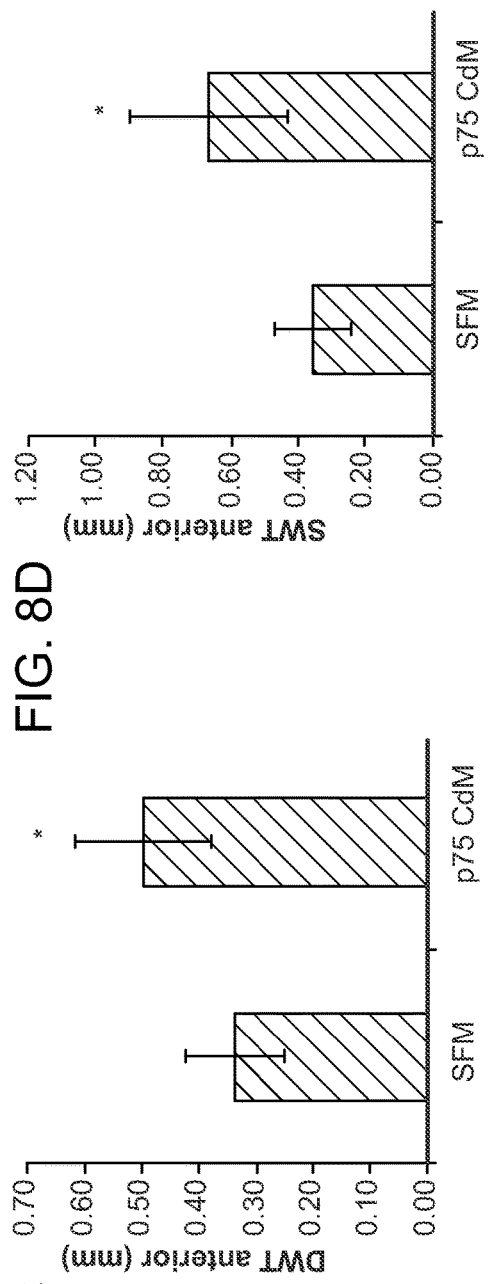
FIG. 8A
FIG. 8C

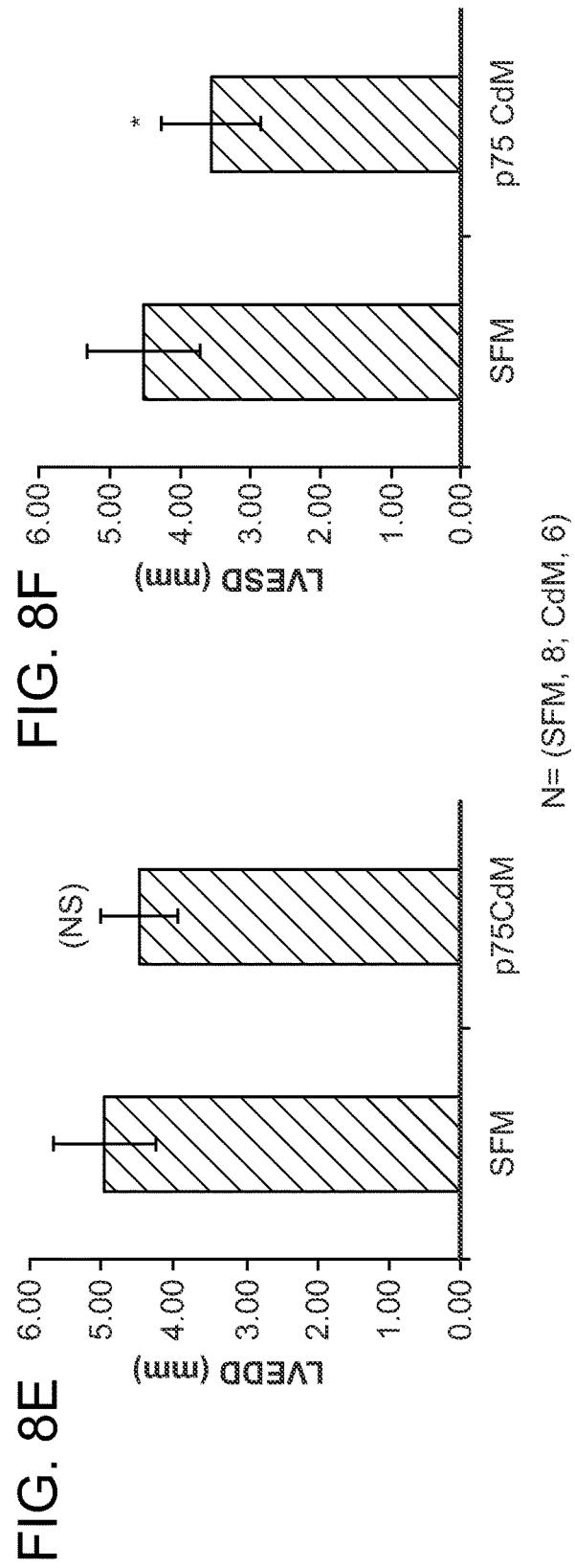

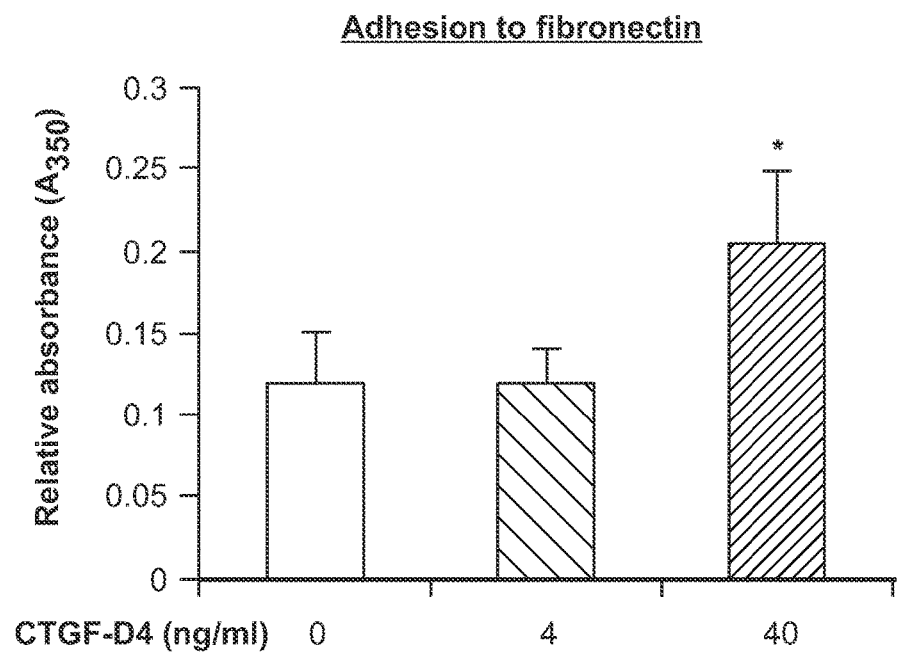
FIG. 14A
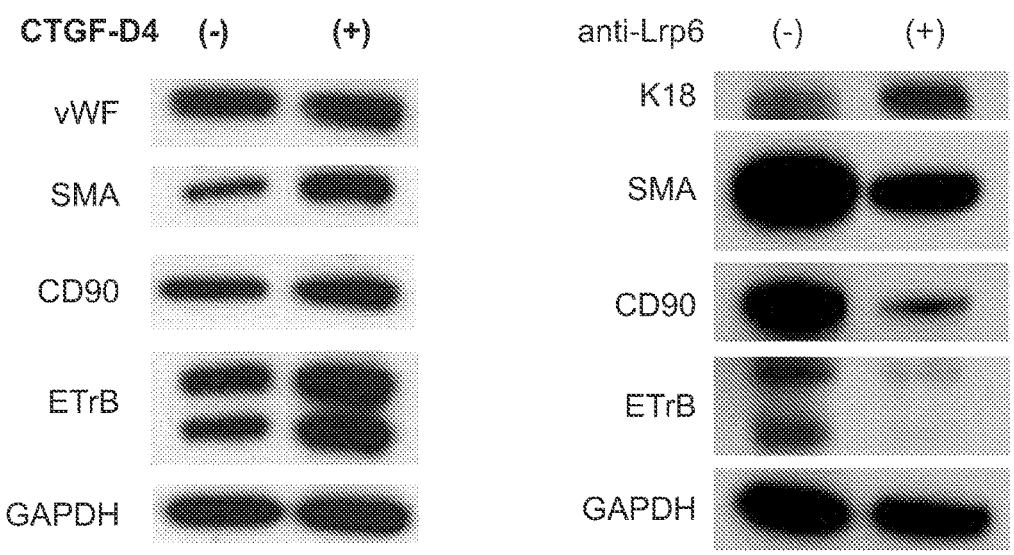
FIG. 14B
FIG. 14C

SEQUENCE LISTING

```
<160> NUMBER OF SEQ ID NOS: 8

<210> SEQ ID NO 1
<211> LENGTH: 349
<212> TYPE: PRT
<213> ORGANISM: Homo sapiens

<400> SEQUENCE: 1

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140
```

```
Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
            165                 170                 175

Pro Ala Leu Ala Ala Tyr Arg Leu Glu Asp Thr Phe Gly Pro Asp Pro
        180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
        210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
                260                 265                 270

Cys Thr Ser Met Lys Thr Tyr Arg Ala Lys Phe Cys Gly Val Cys Thr
            275                 280                 285

Asp Gly Arg Cys Cys Thr Pro His Arg Thr Thr Thr Leu Pro Val Glu
        290                 295                 300

Phe Lys Cys Pro Asp Gly Glu Val Met Lys Lys Asn Met Met Phe Ile
305                 310                 315                 320

Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345

<210> SEQ ID NO 2
<211> LENGTH: 98
<212> TYPE: PRT
<213> ORGANISM: Homo sapiens

<400> SEQUENCE: 2

Met Gly Lys Lys Cys Ile Arg Thr Pro Lys Ile Ser Lys Pro Ile Lys
1               5                   10                  15

Phe Glu Leu Ser Gly Cys Thr Ser Met Lys Thr Tyr Arg Ala Lys Phe
            20                  25                  30

Cys Gly Val Cys Thr Asp Gly Arg Cys Cys Thr Pro His Arg Thr Thr
        35                  40                  45

Thr Leu Pro Val Glu Phe Lys Cys Pro Asp Gly Glu Val Met Lys Lys
    50                  55                  60

Asn Met Met Phe Ile Lys Thr Cys Ala Cys His Tyr Asn Cys Pro Gly
65                  70                  75                  80

Asp Asn Asp Ile Phe Glu Ser Leu Tyr Tyr Arg Lys Met Tyr Gly Asp
                85                  90                  95

Met Ala

<210> SEQ ID NO 3
<211> LENGTH: 135
<212> TYPE: PRT
<213> ORGANISM: Homo sapiens

<400> SEQUENCE: 3

Met Ala Ala Ala Ser Met Gly Pro Val Arg Val Ala Phe Val Val Leu
1               5                   10                  15
```

```
Leu Ala Leu Cys Ser Arg Pro Ala Val Gly Gln Asn Ser Cys Gly Pro
            20                  25                  30

Cys Arg Cys Pro Asp Glu Pro Lys Lys Cys Ile Arg Thr Pro Lys Ile
        35                  40                  45

Ser Lys Pro Ile Lys Phe Glu Leu Ser Gly Cys Thr Ser Met Lys Thr
    50                  55                  60

Tyr Arg Ala Lys Phe Cys Gly Val Cys Thr Asp Gly Arg Cys Cys Thr
65                  70                  75                  80

Pro His Arg Thr Thr Thr Leu Pro Val Glu Phe Lys Cys Pro Asp Gly
                85                  90                  95

Glu Val Met Lys Lys Asn Met Met Phe Ile Lys Thr Cys Ala Cys His
            100                 105                 110

Tyr Asn Cys Pro Gly Asp Asn Asp Ile Phe Glu Ser Leu Tyr Tyr Arg
        115                 120                 125

Lys Met Tyr Gly Asp Met Ala
    130                 135

<210> SEQ ID NO 4
<211> LENGTH: 408
<212> TYPE: DNA
<213> ORGANISM: Homo sapiens

<400> SEQUENCE: 4
atggccgccg ccagtatggg ccccgtccgc gtcgccttcg tggtcctcct cgccctctgc      60
agccggccgg ccgtcggcca gaactgcagc gggccgtgcc ggtgcccgga cgagccaaaa     120
aagtgcatcc gtactcccaa aatctccaag cctatcaagt ttgagctttc tggctgcacc     180
agcatgaaga cataccgagc taaattctgt ggagtatgta ccgacggccg atgctgcacc     240
ccccacagaa ccaccaccct gccggtggag ttcaagtgcc ctgacggcga ggtcatgaag     300
aagaacatga tgttcatcaa gacctgtgcc tgccattaca actgtcccgg agacaatgac     360
atctttgaat cgctgtacta caggaagatg tacggagaca tggcatga                 408

<210> SEQ ID NO 5
<211> LENGTH: 110
<212> TYPE: PRT
<213> ORGANISM: Homo sapiens

<400> SEQUENCE: 5

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 6
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 6

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Asn Gln His Leu Cys Gly Ser His Leu Val Glu Ala Leu Tyr Leu
1               5                   10                  15

Val Cys Gly Glu Arg Gly Phe Phe Tyr Thr Pro Lys Thr
            20                  25

<210> SEQ ID NO 8
<211> LENGTH: 153
<212> TYPE: PRT
<213> ORGANISM: Homo sapiens

<400> SEQUENCE: 8

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150
```

METHODS FOR ENHANCING CARDIAC FUNCTION WITH THE COMBINATION OF CTGF AND INSULIN OR IGF-1

CROSS REFERENCE TO RELATED APPLICATIONS

This application is the U.S. national phase application, pursuant to 35 U.S.C. §371, of PCT international application Ser. No. PCT/US2014/022094, filed Mar. 7, 2014, designating the United States and published in English, which claims priority to and the benefit of U.S. Provisional Application No. 61/775,285, filed Mar. 8, 2013, which is incorporated herein by reference in its entirety.

STATEMENT OF RIGHTS TO INVENTIONS MADE UNDER FEDERALLY SPONSORED RESEARCH

This work was supported by the following grant from the National Institutes of Health, Grant No: HL085210. The government has certain rights in the invention.

SEQUENCE LISTING

The instant application contains a Sequence Listing which has been submitted electronically in ASCII format and is hereby incorporated by reference in its entirety. Said ASCII copy, created on Aug. 11, 2016, is named 167941_010302_SL.txt and is 9,204 bytes in size.

BACKGROUND OF THE INVENTION

Despite recent advances in treating ischemic injuries, stroke and myocardial infarction continue to kill or disable vast numbers of people each year. In the United States alone, 600,000 new myocardial infarctions and 320,000 recurrent attacks occur annually. About 38 percent of the people who experience a myocardial infarction in a given year will die, while many of those who survive will experience some loss in cardiac function.

Certain cell types, including muscle cells and neurons are particularly vulnerable to ischemic injury in connection with myocardial infarction and stroke. Technologies associated with the identification, isolation, and culture of stem/progenitor cells now provides many candidate cells for cell replacement applications in regenerative medicine. Notably, however, transplantation of culture-expanded adult stem/progenitor cells often results in poor cellular engraftment, survival, and migration into sites of tissue injury. As such, current cell replacement strategies for treating myocardial infarction involving the injection of stem/progenitor cells result in modest improvements in cardiac function, at best. Low levels of engraftment, survival, and cell replacement after injection of adult or embryonic stem cells into the injured left ventricle wall are important issues that reduce the potential effectiveness of cell replacement strategies after myocardial infarction. Moreover, intravenous infusion of cultured adult stem/progenitor cells can be accompanied by microembolism and cardiac arrhythmias. Accordingly, improved methods of treating tissue injury, particularly ischemic injuries associated with myocardial infarction, are urgently required.

SUMMARY OF THE INVENTION

As described below, the present invention features compositions and methods for treating or preventing cardiac tissue damage, including damage associated with an ischemic event.

In one aspect, the invention provides a composition containing one or more of connective tissue growth factor (CTGF) and human C-terminal CTGF peptide; and one or more of insulin and IGF-1.

In another aspect, the invention provides a composition containing a human C-terminal CTGF peptide that enhances cardiac progenitor cell survival and/or proliferation.

In still another aspect, the invention provides a method for increasing cardiac cell survival or proliferation, the method involving contacting a cardiac cell at risk of cell death with a composition containing one or more of connective tissue growth factor (CTGF) and human C-terminal CTGF peptide; and one or more of insulin and IGF-1.

In yet another aspect, the invention provides a method for stabilizing or reducing cardiac tissue damage in a subject, the method involving contacting a cardiac cell of the subject with a composition containing one or more of connective tissue growth factor (CTGF) and human C-terminal CTGF peptide; and one or more of insulin and IGF-1, thereby stabilizing or reducing cardiac tissue damage in the subject.

In still another aspect, the invention provides a method for enhancing engraftment of a cardiac cell or progenitor thereof (e.g., an adult cardiac myocyte, adult cardiac endothelial cell, adult cardiac smooth muscle cell, adult cardiac fibroblast, adult cardiac stem cell, adult cardiac progenitor cell, adult vascular stem cell, adult epicardial cell, adult subepicardial cell, adult bone marrow-derived stem or progenitor cell, cardiac derivative from embryonic stem (ES) cells, and/or induced pluripotent stem (iPS) cell), the method involving contacting the cell (i.e., to be primed) with a composition containing one or more of connective tissue growth factor (CTGF) and human C-terminal CTGF peptide; and one or more of insulin and IGF-1, thereby enhancing engraftment.

In another aspect, the invention provides a method for enhancing engraftment of a cardiac cell or progenitor thereof in a subject, the method involving: contacting the cardiac cell or progenitor in vitro with a composition containing one or more of connective tissue growth factor (CTGF) and human C-terminal CTGF peptide; and one or more of insulin and IGF-1, thereby generating a primed cell; and administering the primed cell to the subject, thereby enhancing engraftment of the cell in the subject.

In one aspect, the invention provides a cellular composition containing an isolated cardiac progenitor cell, cardiac stem cell, mesenchymal stem cell or progeny cell thereof contacted with a composition containing one or more of connective tissue growth factor (CTGF) and human C-terminal CTGF peptide; and one or more of insulin and IGF-1.

In another aspect, the invention provides an isolated polynucleotide encoding CTGF-D4.

In still another aspect, the invention provides an isolated polypeptide comprising CTGF-D4.

In yet another aspect, the invention provides an isolated cardiac progenitor cell, cardiac stem cell, mesenchymal stem cell or progeny cell thereof expressing recombinant CTGF-D4. In certain embodiments, the isolated cardiac progenitor cell, cardiac stem cell, mesenchymal stem cell or progeny cell also expresses insulin and/or IGF-1.

In various embodiments of any of the aspects delineated herein, the cardiac cell or progenitor is contacted in vitro or in vivo. In various embodiments of any of the aspects delineated herein, the cardiac cell or progenitor is contacted with the composition or primed cell for 5, 10, 15, 20, 25, 30, 35, 40, 45, 60, 90, 120, 150, 180, 210, 240 min, or 3, 4, 5, or 6 hrs. In various embodiments of any of the aspects delineated herein, the cardiac cell or progenitor is autologous or heterologous. In various embodiments of any of the aspects delineated herein, following contact of the cardiac cell or progenitor in vitro, the cell is administered to a subject.

In various embodiments of any of the aspects delineated herein, the composition or primed cell is administered to a subject directly to a site of cardiac tissue damage or cardiac disease or is administered systemically. In particular embodiments, the composition or primed cell is administered by intra-arterial infusion.

In various embodiments of any of the aspects delineated herein, the method reduces cell death or increases cardiac function. In particular embodiments, the method increases cardiac cell number or reduces cardiac cell death. In various embodiments of any of the aspects delineated herein, the method increases cardiac cell number by at least about 5% compared to a corresponding untreated control cardiac tissue or heart.

In various embodiments of any of the aspects delineated herein, the subject has a disease or disorder selected from the group consisting of myocardial infarction, congestive heart failure, stroke, and ischemia. In various embodiments of any of the aspects delineated herein, the method prevents or ameliorates ischemic damage. In various embodiments of any of the aspects delineated herein, the method reduces apoptosis or increases cell proliferation.

In various embodiments of any of the aspects delineated herein, the method prevents or ameliorates ischemic damage in a cardiac tissue post-myocardial infarction.

Other features and advantages of the invention will be apparent from the detailed description, and from the claims.

DEFINITIONS

By "increasing epicardial cell proliferation" is meant increasing cell division of an epicardial progenitor cell or a cell derived from an epicardial progenitor cell in vivo or in vitro. Increasing epicardial cell proliferation may also include promoting, supporting, or inducing the differentiation and/or migration of epicardial cells. For example, an increase in cell number may be at least about a 5%, 10%, 15%, 20%, 30%, 40%, 50%, 60%, 70%, 80%, 90%, or even 100% increase in the number of epicardial cells relative to the number of cells present in a naturally-occurring, corresponding cardiac tissue or heart.

By "cardiac protective activity" is meant any biological activity that maintains or increases the survival or function of a cardiac cell or cardiac tissue in vitro or in vivo.

By "cardiac function" is meant the biological function of cardiac tissue or heart (e.g., contractile function). Methods for measuring the biological function of the heart are standard in the art (e.g., Textbook of Medical Physiology, Tenth edition, (Guyton et al., W.B. Saunders Co., 2000) and are also described herein. By "increasing in cardiac function" is meant an increase in a biological function of the heart by at least about 5%, 10%, 15%, 20%, 30%, 40%, 50%, 60%, 70%, 80%, 90%, or even 100% relative to the biological function present in a naturally-occurring, corresponding cardiac tissue or heart.

By "cell survival" is meant cell viability.

By "reducing cell death" is meant reducing the propensity or probability that a cell will die. Cell death can be apoptotic, necrotic, or by any other means.

By "cellular factor" is meant any biological agent produced by a cell. While cellular factors isolated from culture media are typically secreted by cells in culture, the scope of the invention is intended to include any factor released from a cultured cell into growth media. In one embodiment, a cellular factor of the invention is secreted by a cell or is released into culture media when a cell breaks open and releases its contents into the growth media. Exemplary cellular factors include connective tissue growth factor (CTGF), human C-terminal CTGF peptide, insulin and IGF-1.

By "secreted cellular factor" is meant any biologically active agent that a cell secretes during in vitro culture.

By "connective tissue growth factor (CTGF) polypeptide" is meant a protein or fragment thereof having at least about 85% identity to NCBI Accession No. NP_001892, or that binds an antibody generated against the CTGF antigen. An exemplary full-length CTGF polypeptide is provided below.

```
                                                          (SEQ ID NO: 1)
  1    mtaasmgpvr vafvvllalc srpavgqncs gpercpdepa prcpagvslv ldgcgccrvc 61    akqlgelcte rdpcdphkgl fcdfgspanr kigvctakdg apcifggtvy rsgesfqssc 121    kyqctcldga vgcmplcsmd vrlpspdcpf prrvklpgkc ceewvcdepk dqtvvgpala 181    ayrledtfgp dptmirancl vqttewsacs ktcgmgistr vtndnascrl ekqsrlcmvr 241    pceadleeni kkgkkcirtp kiskpikfel sgctsmktyr akfcgvctdg rcctphrttt 301    lpvefkcpdg evmkknmmfi ktcachyncp gdndifesly yrkmygdma
```

By "CTGF nucleic acid molecule" is meant a polynucleotide encoding a CTGF polypeptide.

In one preferred embodiment, a CTGF polypeptide is CTGF module 4 (CTGF-D4), which is provided below.

```
                                                          (SEQ ID NO: 2)
  1    mgkkcirtpk iskpikfels gctsmktyra kfcgvctdgr cctphrtttl pvefkcpdge 61    vmkknmmfik tcachyncpg dndifeslyy rkmygdma
```

In another preferred embodiment, a CTGF polypeptide is CTGF-D4 that includes a signal peptide (bold), which is provided below.

```
                                                        (SEQ ID NO: 3)
  1   maaasmgpvr vafvvllalc srpavgqnsc gpercpdepk kcirtpkisk pikfelsgct 61   smktyrakfc gvctdgrcct phrtttlpve fkcpdgevmk knmmfiktca chyncpgdnd 121   ifeslyyrkm ygdma
```

An exemplary CTGF nucleic acid molecule encoding the above CTGF-D4 polypeptide and signal peptide sequence (bold) is provided below.

```
                                                        (SEQ ID NO: 4)
  1   atggccgccg ccagtatggg ccccgtccgc gtcgccttcg tggtcctcct cgccctctgc 61   agccggccgg ccgtcggcca gaactgcagc gggccgtgcc ggtgcccgga cgagccaaaa 121   aagtgcatcc gtactcccaa aatctccaag cctatcaagt ttgagctttc tggctgcacc 181   agcatgaaga cataccgagc taaattctgt ggagtatgta ccgacggccg atgctgcacc 241   ccccacagaa ccaccaccct gccggtggag ttcaagtgcc ctgacggcga ggtcatgaag 301   aagaacatga tgttcatcaa gacctgtgcc tgccattaca actgtcccgg agacaatgac 361   atctttgaat cgctgtacta caggaagatg tacggagaca tggcatga
```

By "insulin polypeptide" is meant a protein or fragment thereof having at least about 85% identity to NCBI Accession No. NP_000198, or that binds an antibody generated against the insulin antigen. An exemplary full-length insulin polypeptide is provided below.

```
                                                        (SEQ ID NO: 5)
  1   malwmrllpl lallalwgpd paaafvnghl cgshlvealy lvcgergffy tpktrreaed 61   lqvggvelgg gpgagslqpl alegslqkrg iveqcctsic slyglenycn
```

In one preferred embodiment, the insulin is a dimer of insulin A-chain and insulin B-Chain of the full-length insulin polypeptide (A-chain: amino acids 90-110; B-chain: amino acids 25-54) linked by 2 disulfide bonds. Active or mature insulin is processed from the full-length insulin polypeptide, also termed preproinsulin. The insulin signal peptide (amino acids 1-24) is cleaved from preproinsulin to generate proinsulin. The proinsulin polypeptide folds in the endoplasmic reticulum, including the formation of intramolecular disulfide bonds. Cleavage of insulin C-chain (amino acids 57-87) from the folded proinsulin polypeptide produces a dimer of the A-chain and B-chain linked by 2 interchain disulfide bonds, which is the mature or active form. The A-chain of the active or mature dimer contains an intrachain disulfide bond. Active insulin is commercially available (Sigma-Aldrich 19278; CAS No. 11061-68-0; MDL No. MFCD00131380). Insulin A- and B- chain sequences are provided below.

```
      Insulin A-chain:
                                                        (SEQ ID NO: 6)
  1   givegcctsi cslyglenyc n
```

```
      Insulin B-chain:
                                                        (SEQ ID NO: 7)
  1   vnghlcgshl vealylvcge rgffytpkt
```

By "insulin nucleic acid molecule" is meant a polynucleotide encoding an insulin polypeptide.

By "Insulin-like growth factor 1 (IGF-1) polypeptide" is meant a protein or fragment thereof having at least about 85% identity to NCBI Accession No. NP_000609, or that binds an antibody generated against the IGF-1 antigen. An exemplary full-length IGF-1 polypeptide is provided below.

```
                                                        (SEQ ID NO: 8)
  1   mgkisslptq lfkccfcdfl kvkmhtmsss hlfylalcll tftssatagp etlcgaelvd 61   alqfvcgdrg fyfnkptgyg sssrrapqtg ivdeccfrsc dlrrlemyca plkpaksars 121   vraqrhtdmp ktgkevhlkn asrgsagnkn yrm
```

By "IGF-1 nucleic acid molecule" is meant a polynucleotide encoding a IGF-1 polypeptide.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean " includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "deficiency of a particular cell-type" is meant fewer of a specific set of cells than are normally present in a tissue or organ not having a deficiency. For example, a deficiency is a 5%, 10%, 15%, 20%, 30%, 40%, 50%, 60%, 70%, 80%, 90%, or even 100% deficit in the number of cells of a particular cell-type (e.g., cardiomyocytes, epicardial progenitor cells, embryonic stem cells, endothelial cells, endothelial precursor cells, fibroblasts, neurons, adipocytes) relative to the number of cells present in a naturally-occurring, corresponding tissue or organ. Methods for assaying cell-number are standard in the art, and are described in (Bonifacino et al., Current Protocols in Cell Biology, Loose-leaf, John Wiley and Sons, Inc., San Francisco, Calif., 1999; Robinson et al., Current Protocols in Cytometry Loose-leaf, John Wiley and Sons, Inc., San Francisco, Calif., October 1997).

"Derived from" as used herein refers to the process of obtaining a cell from a subject, embryo, biological sample, or cell culture.

"Detect" refers to identifying the presence, absence or amount of the object to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include any disease or injury that results in a reduction in cell number or biological function, including ischemic injury, such as stroke, myocardial infarction, or any other ischemic event that causes tissue damage.

By "effective amount" is meant the amount of a required to ameliorate the symptoms of a disease relative to an untreated patient. The effective amount of active compound(s) used to practice the present invention for therapeutic treatment of a ischemic injury varies depending upon the manner of administration, the age, body weight, and general health of the subject. Ultimately, the attending physician or veterinarian will decide the appropriate amount and dosage regimen. Such amount is referred to as an "effective" amount.

By "engraftment" is meant the integration of an exogenous cell into a tissue of a subject. In one embodiment, a primed cell (e.g., cardiac progenitor cell) is engrafted into the heart of a subject in need thereof (e.g., post-myocardiac infarction).

By "fragment" is meant a portion of a polypeptide or nucleic acid molecule. This portion contains, preferably, at least 10%, 20%, 30%, 40%, 50%, 60%, 70%, 80%, 85%, 90%, 95%, or more of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "increase" is meant to alter positively by at least 5%. An alteration may be by 5%, 10%, 25%, 30%, 50%, 75%, or even by 100%.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis. When a cellular factor is "isolated" from a cultured epicardial progenitor cell the cellular factor is typically separated from cells and cellular debris. It need not be purified to homogeneity. In fact, the composition comprising an isolated cellular factor typically comprises any number of cellular factors whose presence contributes to the biological activity (e.g., growth promoting, survival promoting, or proliferation promoting activity) of the composition. In one embodiment, a composition of the invention comprises or consists of conditioned media from which cells and cellular debris have been removed.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reduce" is meant to alter negatively by at least 5%. An alteration may be by 5%, 10%, 25%, 30%, 50%, 75%, or even by 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "primed cell" is meant a cell that is contacted with any one or more of connective tissue growth factor (CTGF), human C-terminal CTGF peptide, insulin and/or IGF-1 prior to administration to a subject (e.g., for engraftment in the subject). In various embodiments, a primed cell is contacted with CdM. In various embodiments, a primed cell is contacted with any one or more of connective tissue growth factor (CTGF), human C-terminal CTGF peptide, insulin and/or IGF-1 for 5, 10, 15, 20, 25, 30, 35, 40, 45, 60, 90, 120, 150, 180, 210, 240 min, or 3, 4, 5, or 6 hrs., prior to administration for engraftment in a subject By "repair" is meant to ameliorate damage or disease in a tissue or organ.

By "tissue" is meant a collection of cells having a similar morphology and function.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

BRIEF DESCRIPTION OF THE DRAWINGS

FIGS. 1A-1C depict proliferation of adult rat CPCs was induced by human stromal cell CdM. FIG. 1A is a graph showing time course changes in the numbers of CPCs treated with CdM or SFM (left panel) and phase contrast images of CSCs, CPCs in CPC growth medium, and CPCs treated with CdM from MSCs, p75MSCs, or fibroblasts or SFM for 8 days (magnification, 10×). CPC growth medium=CSC medium with 2% FBS. Scale bars=50 μM (right panel). CdM was assayed from 2 different donors for each cell type. The control cell number (48,896 cells) was regarded as 100%. Data are mean±SEM, n=3 to 7. *, P<0.0001 vs baseline; **, P<0.01 vs baseline; †, P<0.0001 vs SFM. FIG. 1B is a graph showing quantification of BrdU-positive CPCs after immuno-cytochemistry. Data are mean±SEM, n=3, CdM from different donors were assayed for each cell type. Inset: Immunoblot for Ki67 in CPCs (molecular weight, 359 kDa: lane 1, SFM; lane 2, 1× MSC CdM; lane 3, p75MSC CdM; lane 4, 1× fibroblast CdM). *, P<0.05 vs SFM; **, P<0.01 vs SFM. FIG. 1C is a graph showing that MSC CdM did not grow adult rat cardiac fibroblasts. Data are mean±SEM, n=3. The control cell number (34,606 cells) was regarded as 100%. *, P<0.0001 vs baseline. CdM, conditioned medium. SFM, serum-free α-MEM. GM, CPC growth medium (CSC medium with 2% FBS).

FIG. 2A is a graph showing a dose-dependent effect of 10×-concentrated CdM on CPC proliferation. CPC growth in 1× CdM from one MSC donor and one p75MSC donor is shown for reference. Control cell number (60,191 cells) was regarded as 100%. Data are mean±SEM, n=3. 10× CdM from 2 different donors was assayed for each cell type. *, P<0.0001 vs baseline; **, P<0.0001 vs day 4; †, P<0.05 vs day 8. CdM, conditioned medium. FIG. 2B is a graph showing growth of CPCs in p75MSC CdM is dependent on signaling through STAT3 and abolished by incubation with the specific STAT3 inhibitor, "Stattic" (10 μM). *, P<0.001 vs DMSO vehicle on day 2; **, P<0.001 vs. DMSO vehicle on day 4. FIG. 2C is a graph showing time course changes in the numbers of CPCs treated with SFM supplemented with various growth factors (EGF, bFGF, and LIF; 10 ng/ml) and in the absence of Insulin-Transferrin-Selenium. Control cell number (64,026 cells) was regarded as 100%. Data are mean±SEM, n=3. *, P<0.01 SFM and SFM+EGF+FGF vs baseline; **, P<0.001 SFM, SFM+EGF+FGF, and SFM+LIF+EGF+FGF vs baseline. Data for growth in 1× CdM from one MSC donor is shown for reference.

FIG. 3A shows immunoblotting for phosphorylated STAT3 (p-STAT3) and total STAT3 (T-STAT3) in CPCs (molecular weight, 86 kDa) (left panel) and quantification of STAT3 phosphorylation levels (n=3) (right panel). Beta-actin levels indicate loading controls. The corrected values in SFM on day1 and 2 were designated as 1, n=3. *, P<0.05 vs SFM. FIG. 3B shows images of immunofluorescent staining for p-STAT3 and T-STAT3 in CPCs (magnification×400). Note: p-STAT3 localizes to CPC nuclei. Blue indicates DAPI nuclear staining. FIG. 3C shows immunoblotting for phosphorylated Akt (p-Akt) and total Akt (T-Akt) in CPCs (molecular weight, 62 kDa). FIG. 3D is a graph showing an inhibitory effect of AG490 (10 μM) on CPC growth and survival in stromal cell CdM for 48 hrs.

Data are mean±SEM, n=3 to 6. Control cell numbers (121,863 cells in MSC CdM, 115,342 cells in p75MSC CdM, and 118,682 cells in fibro CdM) were regarded as 100%. *, P<0.0001 vs control. FIG. 3E is a graph showing inhibitory effects of AG490 (10 µM) and LY294002 (10 µM) on CPCs incubated with 1× CdM for 48 hrs. Data are mean±SEM, n=3 to 6. The control cell numbers (121,863 cells) were regarded as 100%. *, P<0.0001 vs control; **, P<0.01 vs AG; †, P<0.05 vs LY. Con: control, DMSO. AG: AG490, Jak2/STAT3 pathway inhibitor. LY: LY294002, inhibitor of PI3K/Akt pathway. A+L: AG490+LY294002. CdM, conditioned medium. SFM, serum-free α-MEM. GM, CPC growth medium (CSC medium with 2% FBS).

FIG. 4A is a graph showing CPC numbers in GM, SFM and CdM after exposure to chronic hypoxia. Control cell number (139,616 cells) was regarded as 100%. Data are mean±SEM, n=3, CdM from 2 different donors was assayed for each cell type. *, P<0.05 vs SFM; **, P<0.01 vs SFM. FIG. 4B is a graph depicting STAT3 inhibition with AG490 (10 µM) blocks CPC protection conferred by CdM during hypoxia. Control cell numbers (56,559 cells in MSC CdM, 92,120 cells in p75MSC CdM, and 74,511 cells in fibro CdM) were regarded as 100%. *, P<0.0001 vs CdM. AG: AG490, Jak2/STAT3 pathway inhibitor. FIG. 4C is a graph showing survival of CPCs in p75MSC CdM and under hypoxic conditions for 48 hrs is dependent on signaling through STAT3 and abolished by incubation with the STAT3-specific inhibitor, "Stattic" (10 µM). **, P<0.001 vs DMSO vehicle with 1× or 10× CdM. CdM, conditioned medium. SFM, serum-free α-MEM. GM, CPC growth medium (CSC medium with 2% FBS).

FIG. 5A depicts images of immunofluorescent staining for α-SA, α-sarcomeric actin; SMA, α-smooth muscle actin; and vWF, von Willebrand factor. Left panels (Baseline) show the CPCs in growth medium 3 days after plating, and the right panels show CPCs expanded in CdM for 4 days. Scale bars=100 µM. FIG. 5B depicts quantification of % positive cells for α-SA, SMA, and vWF. Data are mean±SEM, n=3. CdM, conditioned medium.

FIG. 6A depicts TUNEL staining of heart sections from vehicle (SFM-treated). Scale bars=100 µM. FIG. 6B depicts TUNEL staining of heart sections from CdM-treated C57bl6 mice. At 24 hrs after LAD ligation, 200 µl of SFM or 30× p75MSC CdM was slowly infused into the left ventricle lumen (intra-arterial delivery). Scale bars=100 µM. FIG. 6C depicts quantification of TUNEL cells in heart sections of animals that received intra-arterial infusion of SFM or 30× p75MSC CdM 24 hrs after MI.

FIGS. 8A-8E are graphs depicting that intra-arterial infusion of 30× p75MSC CdM 24 hrs after MI improved cardiac function 1 week after MI. FIG. 8A is a graph showing that P75 CdM treatment significantly improved wall motion (thickening) after MI. Echocardiography score was determined with a 13 segment model similar to the American Society of Echocardiography's 16 segment model. The best possible score is a 13 (full motion) and the worst possible score is a 39 (akinetic). FIG. 8B is a graph showing that P75 CdM infusion significantly increased (preserved) the percent of fractional shortening after MI. FIG. 8C is a graph showing that P75 CdM significantly increased (preserved) anterior wall thickness in diastole after MI. FIG. 8D is a graph showing that P75 CdM treatment significantly increased (preserved) anterior wall thickness in systole after MI. FIG. 8E is a graph showing that there was no significant difference in end diastolic diameter of the left ventricle with or without p75 CdM treatment after MI. FIG. 8F is a graph showing that P75 CdM infusion significantly decreased the end systolic diameter of the left ventricle after MI. *, P≤0.05.; **, P≤0.01. For all data, SFM, n=8; p75 CdM, n=6. Echocardiography was performed using a VisualSonics Vevo 770 system.

FIG. 9A is an image of the largest cell graft for control rats (n=5), at 1 week after MI and injections of CSCs/SFM. Yellow autofluorescence indicates host-derived myocytes. Scale bar=100 µM. FIGS. 9B-9D depict images of sub-epicardial grafts from three different rats, 1 week after MI and injections of CSCs/CdM (n=6). Scale bars=100 µM. Ki67 staining (red) in FIG. 9C shows proliferating GFP CSC derivatives in sub-epicardial tissue after CSC/CdM injections. FIGS. 9D and 9D' are images showing that in hearts treated with CSCs/CdM, GFP$^+$ cells migrated between apparently healthy cardiac myocytes in order to reach distant zones of necrotic myocardium with infarction. In FIG. 9D, white arrows indicate change in CSC orientation during migration from sub-epicardium into myocardium after MI; compare to orientation in FIG. 9B. Scale bar=50 µM. In FIG. 9D' dashed white line indicates edge of infarction. Scale bar=100 µM. FIG. 9E is an image showing that after CdM-priming, GFP CSC derivatives migrated into areas of necrosis with few remaining viable myocytes. Scale bar=50 µM. FIG. 9F is an image showing that CdM-primed CSC derivatives differentiated into CD31-positive (red) vascular endothelial cells to repair blood vessels. Scale bar=100 µM. FIG. 9G is an image showing CdM-primed CSC derivatives differentiated into smooth muscle alpha actin-positive (SMA, red) smooth muscle cells and myofibroblasts (arrows indicate co-localizations with GFP). Scale bar=100 µM. FIG. 9H is a graph depicting quantification of GFP cells from individual tissue sections with the most engraftment in hearts that received CSCs/SFM (rats 1-5) or CSCs/CdM (rats 6-11). Note: Counting was stopped after 20,000 GFP$^+$ cells for two of the CSC/CdM-treated rats, but observed thousands of additional GFP$^+$ cells.

FIGS. 12A-12C depict priming of cultured CSCs in CTGF-D4 and Insulin promoted graft success after MI. FIGS. 12A and 12A' are images showing few control rats (1/7) injected with CSCs primed for 30 min. in vehicle (SFM with 1% BSA) had detectable GFP+ cells at 1 week after MI and sub-epicardial injections. Scale bars=50 µM in FIG. 12A and 100 µM in FIG. 12A'. Note: GFP+ cells of control rats did not exit sub-epicardial graft site. All rats (5/5) that received CSCs primed with CTGF-D4 (3 ng/ml)/Insulin (30 ng/ml) demonstrated robust engraftment of GFP+ cells at 1 week after MI (FIGS. 12B, 12B', 12C and 12C'). FIG. 12B depicts sub-epicardial engraftment of GFP+ cells 1 week after MI in a representative animal that received CSCs primed with CTGF-D4/Insulin. Scale bar=50 μM. FIG. 12B' depicts extensive migration/integration of GFP+ cells 1 week after MI in a representative animal that received CSCs primed with CTGF-D4/Insulin. White dashes indicate infarct border. Area beyond dashes has few viable myocytes that remain from host. Scale bar=50 μM. FIG. 12C depicts engraftment of GFP+ cells 1 week after MI in a second representative animal that received CSCs primed with CTGF-D4/Insulin. Image demonstrates integration into area with infarction. Scale bar=50 μM. FIG. 12C' depicts extensive migration/integration of GFP+cells 1 week after MI in the second representative animal that received CSCs primed with CTGF-D4/Insulin. FITC channel shows extent of migration into infarct. White dashes indicate infarct border. Area beyond dashes has few viable myocytes that remain from host. Scale bar=50 μM.

FIGS. 12A-12D depict priming of cultured CSCs in CTGF-D4 and Insulin promoted graft success after MI. FIGS. 12A and 12A' are images showing that few control rats (1/7) injected with CSCs primed for 30 min. in vehicle (SFM with 1% BSA) had detectable GFP+ cells at 1 week after MI and sub-epicardial injections. Scale bars=50 μM in FIG. 12A and 100 μM in FIG. 12A'. Note: GFP+ cells of control rats did not exit sub-epicardial graft site. All rats (5/5) that received CSCs primed with CTGF-D4 (3 ng/ml)/Insulin (30 ng/ml) demonstrated robust engraftment of GFP+ cells at 1 week after MI (FIGS. 12B, 12B', 12C and 12C'). FIG. 12B depicts sub-epicardial engraftment of GFP+ cells 1 week after MI in a representative animal that received CSCs primed with CTGF-D4/Insulin. Scale bar=50 μM. FIG. 12B' depicts extensive migration/integration of GFP+ cells 1 week after MI in a representative animal that received CSCs primed with CTGF-D4/Insulin. White dashes indicate infarct border. Area beyond dashes has few viable myocytes that remain from host. Scale bar=50 μM. FIG. 12C depicts engraftment of GFP+ cells 1 week after MI in a second representative animal that received CSCs primed with CTGF-D4/Insulin. Image demonstrates integration into area with infarction. Scale bar=50 μM. FIG. 12C' depicts extensive migration/integration of GFP+ cells 1 week after MI in the second representative animal that received CSCs primed with CTGF-D4/Insulin. FITC channel shows extent of migration into infarct. White dashes indicate infarct border. Area beyond dashes has few viable myocytes that remain from host. Scale bar=50 μM.

FIG. 13A depicts Western blots for Lrp5/6 and phosphorylated GSK3β (p- GSK3β) in rat EPDC lysates. EPDCs were incubated in serum-free medium (SFM) or p75-CdM for 30 min. FIG. 13B consists of a graph depicting the dose-response effect of CTGF-D4 on p- GSK3β in EPDCs (left panel) and an image of nuclear localization of β-catenin in EPDCs after CTGF-D4 exposure (40 ng/ml) (right panel). FIG. 13C is a graph depicting that Dkk-1 significantly reduced protection of EPDCs by CTGF-D4 under hypoxic conditions (1% oxygen, 48 hrs). FIG. 13D is a graph depicting that anti-Lrp5/6 significantly reduced protection of EPDCs by CTGF-D4 under hypoxic conditions (1% oxygen, 48 hrs). FIG. 13E is a graph depicting that an antibody that specifically binds Lrp6 significantly reduced protection of EPDCs by CTGF-D4 under hypoxic conditions (1% oxygen, 48 hrs). FIG. 13F is an image showing that EPDCs graft and migrate into the heart after MI (vertical arrow: subepicardial injection site; horizontal arrows: migration at various time points). FIG. 13G is an image show that adding blocking antisera to Lrp6 to the CTGF-D4/Insulin priming mix substantially reduced the number of grafted EPDCs when hearts were examined at 1 week after MI (red: control cells labeled with non-specific IgG; green: anti-Lrp6 cells (green). FIG. 1H FIG. 13H is an image showing the difference in the number of control cells (non-specific IgG, red) and anti-Lrp6 cells (green) at locations distal to the subepicardial graft site. FIG. 13I is a graph depicting removal of CTGF from p75-CdM by antibody pull-down FIG. 13J is a graph depicting decreased expression of CTGF in p75-CdM by lentiviral transduction of human p75MSCs with shRNA to CTGF.

FIG. 14 depicts that CTGF-D4 increased adhesion of EPDCs to fibronectin and the expression of markers of differentiation and adhesion/migration. FIG. 14A is a graph depicting that CTGF-D4 increased adhesion of EPDCs to fibronectin. FIG. 14B are Western blots showing the effects of CTGF-D4 on markers of differentiation (vWF, SMA) and adhesion/migration (CD90, ETrB). FIG. 14C are Western blots showing that adding Lrp6 to medium containing CTGF-D4 altered the expression of markers of differentiation (vWF, SMA) and adhesion/migration (CD90, ETrB). Addition of Lrp6 neutralizing antisera to medium containing CTGF-D4 at the same dose as in (FIG. 14B) reversed EMT-like differentiation and instead promoted expression of Keratin, an epithelial cell marker.

FIG. 15 depicts that epicardial-derived cell (EPDC) CdM provided vascular protection.

DETAILED DESCRIPTION OF THE INVENTION

Figure 1:
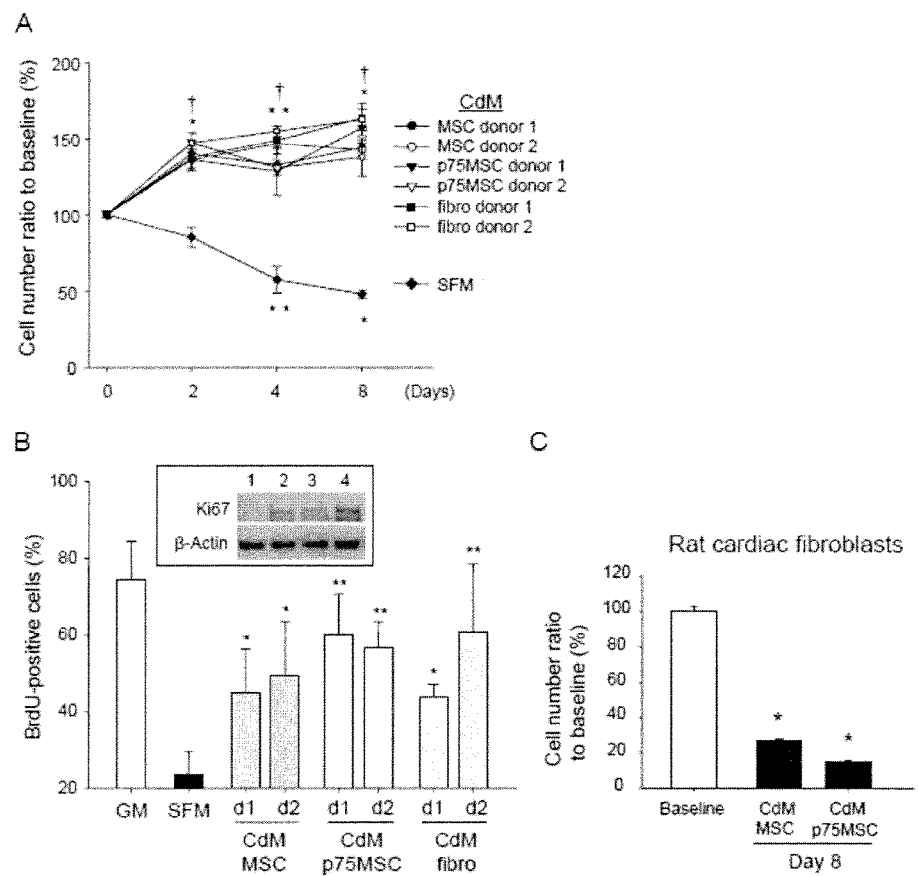

The invention features compositions comprising (a) one or more of connective tissue growth factor (CTGF) and human C-terminal CTGF peptide; and (b) one or more of insulin and IGF-1; and methods of using such compositions to reduce cardiac tissue damage associated with an ischemic event or to enhance engraftment of a cell in a cardiac tissue.

The present invention is based, at least in part, on the discoveries that priming of cells for engraftment in p75MSC CdM or a defined combination of CTGF-D4, insulin, and/or IGF-1 provides a useful way to boost graft success for clinical application of CSCs or cultured stem/progenitor cells derived from other tissues or sources. Accordingly, the invention provides therapeutic and prophylactic compositions comprising agents secreted by mesenchymal stem cells (e.g., CTGF, insulin, and IGF-1) and methods of using such compositions to reduce cardiac cell death, preserve cardiac function after an ischemic event, and to generally prevent cardiac damage and promote cardiac healing or regeneration.

Mesenchymal Stem Cells

Paracrine activity from mesenchymal cells such as fibroblasts and other stromal cells promotes tissue repair after injury and also regulates, in part, stem cell niches. In the bone marrow, endothelial cells and stromal derivatives from non-hematopoietic progenitor cells (multipotent stromal cells, MSCs) support hematopoietic stem cells (HSCs) by providing critical structural and regulatory components of the hematopoietic niche. The niche components include cellular substrate, e.g. extracellular matrix, as well as multiple growth factors, cytokines, and hormones that influence HSC self-renewal, proliferation, survival, and function. Due to their supportive roles, feeder layers of stromal cells (e.g. MSCs or fibroblasts) are commonly used to support the culture of HSCs, other types of adult stem/progenitor cells, and ES cells.

Human bone marrow contains a subpopulation of MSC that can be isolated by magnetic-activated cell sorting against CD271 (p75 low-affinity nerve growth factor receptor, p75MSCs). Human p75MSCs secrete diverse growth factors and cytokines that promote cell survival, angiogenesis, and stem cell engraftment. In transplantation studies, co-infusion of human HSCs and p75MSCs into immunodeficient mice provided a 10-23 fold improvement in multilineage engraftment of bone marrow compared with co-infusion of HSCs and typical (non-selected) human MSCs. $CD271^+$ cells characteristics of bone marrow p75MSCs are rapidly mobilized into the blood of patients with acute MI. Without being bound to a particular theory, it was hypothesized that circulating $CD271^+$ cells participate in cardiac repair/remodeling after myocardial infarction, in part through paracrine activity. Experiments were perfomed to investigate the effects of stromal cell-derived ligands on cardiac stem/progenitor cells (CSCs/CPCs). It was found that conditioned medium (CdM) from human p75MSCs supported the proliferation and survival of adult rat CSCs/CPCs. Furthermore, priming of CSCs in p75MSC CdM for 30 min. prior to transplantation markedly improved CSC grafts after MI. By screening p75MSC CdM for molecules that protected CPCs under hypoxic conditions, two ligands with synergistic effects on CSC survival, CTGF and Insulin, were identified. Priming of CSCs with a defined combination of human CTGF C-terminal peptide (domain 4) and Insulin promoted graft success after MI. Short-term priming of human CSCs with p75MSC CdM or CTGF-D4 and Insulin/IGF-1 may improve graft success and cardiac regeneration in patients with myocardial infarction.

Insulin and Insulin Growth Factor 1 (IGF-1)

Priming in IGF-1 was shown to improve the survival of cardiac cell grafts with adult and embryonic stem cells. Cultured adult rat CPCs were protected by Insulin or IGF-1 during hypoxia. Insulin and Insulin-like growth factor 1 (IGF-1) bind to tyrosine kinase holoreceptors and promote cell survival and proliferation by signaling through the PI3K/Akt and Ras/MAP kinase pathways. Partial functional redundancy for Insulin and IGF-1 signaling is evidenced by signaling through receptor heterodimers IR/IGF-1R and bidirectional cross-talk between ligands/receptors. Although human p75MSC CdM did not contain detectable IGF-1, it had sufficient residual bovine Insulin to significantly improve CPC survival under hypoxic conditions. CdM contains Insulin because MSCs actively sample their environment and internalize fetal calf serum components such as albumin, IgG, and Insulin from their growth medium. Despite washing, they release some components back into the base medium used for CdM production.

Connective Tissue Growth Factor (CTGF)

CTGF is a secreted "matricellular" protein with multiple functions in mammalian development and tissue remodeling/repair after injury, including angiogenesis and fibrosis. During pancreatic development, CTGF promotes the proliferation of beta cell progenitors in islets. Cardiac expression of CTGF increases significantly after MI and it is expressed by interstitial fibroblasts and cardiac myocytes. By interacting with the extracellular matrix, integrins and several cell surface receptors (e.g. LRP-1, LRP-6, TrkA), CTGF mediates numerous cellular functions including: adhesion, proliferation, migration, differentiation, and survival. To regulate coincident processes after injury such as angiogenesis and fibrosis, CTGF physically associates with numerous other secreted proteins including VEGFA, Slit3, von Willebrand Factor, PDGF-B, BMP-4, IGF-1, IGF-2, TGF alpha and TGF beta. CTGF controls fibrosis in multiple tissues after injury, in part, by interacting with TGF beta, IGF-1 or IGF-2 and promoting the differentiation of fibroblasts into myofibroblasts. The N-terminal (1st) and 2nd domains of CTGF interact with IGFs and TGF beta or BMP4, respectively. Notably, due to its numerous binding partners, the effects of CTGF are context-dependent. In the presence of cellular mitogens such as EGF, CTGF does not induce fibrosis, even when pro-fibrotic mediators like TGF beta or IGF-2 are present. C-terminal domain of CTGF (CTGF-D4) and Insulin were found to act in synergy to promote the proliferation and survival of cultured CPCs under hypoxic conditions. Furthermore, a defined combination of CTGF-D4 and Insulin promoted graft success with adult CSCs. Importantly, the CTGF-D4/Insulin priming method described herein is unlikely to promote myofibroblast differentiation or fibrosis from transplanted CSCs as CTGF-D4 is known to promote cell adhesion and proliferation, but lacks N-terminal functions in fibrosis.

Formulations

In one embodiment, a composition of the invention comprises or consists essentially of (a) one or more of connective tissue growth factor (CTGF) and human C-terminal CTGF peptide; and (b) one or more of insulin and IGF-1. In another embodiment, a composition of the invention comprises a cell contacted with (a) one or more of connective tissue growth factor (CTGF) and human C-terminal CTGF peptide; and (b) one or more of insulin and IGF-1.

The biologically active agents present in the conditioned media, the cells, or a combination thereof, can be conveniently provided to a subject as sterile liquid preparations, e.g., isotonic aqueous solutions, suspensions, emulsions, dispersions, or viscous compositions, which may be buffered to a selected pH. Cells and agents of the invention may be provided as liquid or viscous formulations. For some applications, liquid formations are desirable because they are convenient to administer, especially by injection. Where prolonged contact with a tissue is desired, a viscous composition may be preferred. Such compositions are formulated within the appropriate viscosity range. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof. Sterile injectable solutions are prepared by compositions comprising a secreted cellular factor isolated from cultures of stromal or epicardial progenitor cells in the required amount of the appropriate solvent with various amounts of the other ingredients, as desired. Such compositions may be in admixture with a suitable carrier, diluent, or excipient, such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells or agents present in their conditioned media.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent, such as methylcellulose. Other suitable thickening agents include, for example, xanthan gum, carboxymethyl cellulose, hydroxypropyl cellulose, carbomer, and the like. The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form). Those skilled in the art will recognize that the components of the compositions should be selected to be chemically inert.

Compositions comprising (a) one or more of connective tissue growth factor (CTGF) and human C-terminal CTGF peptide; and (b) one or more of insulin and IGF-1 or cells contacted with such agents are administered in an amount required to achieve a therapeutic or prophylactic effect. Such an amount will vary depending on the conditions. Typically, biologically active cellular factors present will be purified and subsequently concentrated so that the protein content of the composition is increased by at least about 5-fold, 10-fold or 20-fold over the amount or protein originally present in the media. In other embodiments, the protein content is increased by at least about 25-fold, 30-fold, 40-fold or even by 50-fold. Preferably, the composition comprises an effective amount of (a) one or more of connective tissue growth factor (CTGF) and human C-terminal CTGF peptide; and (b) one or more of insulin and IGF-1.

The precise determination of what would be considered an effective dose is based on factors individual to each subject, including their size, age, sex, weight, and condition of the particular subject. Dosages can be readily ascertained by those skilled in the art from this disclosure and the knowledge in the art.

Optionally, the methods of the invention provide for the administration of a composition of the invention to a suitable animal model to identify the dosage of the composition(s), concentration of components therein and timing of administering the composition(s), which elicit tissue repair, reduce cell death, or induce another desirable biological response. Such determinations do not require undue experimentation, but are routine and can be ascertained without undue experimentation.

Methods of Delivery

Compositions comprising (a) one or more of connective tissue growth factor (CTGF) and human C-terminal CTGF peptide; and (b) one or more of insulin and IGF-1 or cells contacted with such agents may be delivered to a subject in need thereof. Modes of administration include intramuscular, intra-cardiac, oral, rectal, topical, intraocular, buccal, intravaginal, intracisternal, intra-arterial, intracerebroventricular, intratracheal, nasal, transdermal, within/on implants, e.g., fibers such as collagen, osmotic pumps, or parenteral routes. The term "parenteral" includes subcutaneous, intravenous, intramuscular, intraperitoneal, intragonadal or infusion.

The compositions can be administered via localized injection, including catheter administration, systemic injection, localized injection, intravenous injection, or parenteral administration. When administering a therapeutic composition of the present invention, it will generally be formulated in a unit dosage injectable form (solution, suspension, emulsion). Dosages can be readily adjusted by those skilled in the art (e.g., a decrease in purity may require an increase in dosage). Compositions of the invention can be introduced by injection, catheter, or the like. Compositions of the invention include pharmaceutical compositions comprising cellular factors of the invention and a pharmaceutically acceptable carrier. Administration can be autologous or heterologous.

If desired, biologically active agents present in conditioned media are incorporated into a polymer scaffold to promote tissue repair, cell survival, proliferation in a tissue in need thereof. Polymer scaffolds can comprise, for example, a porous, non-woven array of fibers. The polymer scaffold can be shaped to maximize surface area, to allow adequate diffusion of nutrients and growth factors to a cell of the invention. Polymer scaffolds can comprise a fibrillar structure. The fibers can be round, scalloped, flattened, star-shaped, solitary or entwined with other fibers. Branching fibers can be used, increasing surface area proportionately to volume.

Unless otherwise specified, the term "polymer" includes polymers and monomers that can be polymerized or adhered to form an integral unit. The polymer can be non-biodegradable or biodegradable, typically via hydrolysis or enzymatic cleavage. The term "biodegradable" refers to materials that are bioresorbable and/or degrade and/or break down by mechanical degradation upon interaction with a physiological environment into components that can be metabolized or excreted, over a period of time from minutes to three years, preferably less than one year, while maintaining the requisite structural integrity. As used in reference to polymers, the term "degrade" refers to cleavage of the polymer chain, such that the molecular weight stays approximately constant at the oligomer level and particles of polymer remain following degradation.

Materials suitable for polymer scaffold fabrication include polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, teflon®, nylon silicon, and shape memory materials, such as poly(styrene-block-butadiene), polynorbornene, hydrogels, metallic alloys, and oligo(ε-caprolactone)diol as switching segment/oligo(p-dioxyanone)diol as physical crosslink. Other suitable polymers can be obtained by reference to The Polymer Handbook, 3rd edition (Wiley, N.Y., 1989).

Methods for Evaluating Therapeutic Efficacy

In one approach, the efficacy of the treatment is evaluated by measuring, for example, the biological function of the treated organ (e.g., cardiac cell function). Such methods are standard in the art and are described, for example, in the Textbook of Medical Physiology, Tenth edition, (Guyton et al., W.B. Saunders Co., 2000). In particular, a method of the present invention, increases the biological function of a tissue or organ by at least 5%, 10%, 20%, 40%, 50%, 60%, 70%, 80%, 90%, 100%, 150%, 200%, or even by as much as 300%, 400%, or 500%. Preferably, the tissue is cardiac tissue and, preferably, the organ is heart.

In another approach, the therapeutic efficacy of the methods of the invention is assayed by measuring an increase in cell number in the treated or transplanted tissue or organ as compared to a corresponding control tissue or organ (e.g., a tissue or organ that did not receive treatment). Preferably, cell number in a tissue or organ is increased by at least 5%, 10%, 20%, 40%, 60%, 80%, 100%, 150%, or 200% relative to a corresponding tissue or organ. Methods for assaying cell proliferation are known to the skilled artisan and are described, for example, in Bonifacino et al., (Current Protocols in Cell Biology Loose-leaf, John Wiley and Sons, Inc., San Francisco, Calif.). For example, assays for cell proliferation may involve the measurement of DNA synthesis during cell replication. In one embodiment, DNA synthesis is detected using labeled DNA precursors, such as [3H]-Thymidine or 5-bromo-2*-deoxyuridine [BrdU], which are added to cells (or animals) and then the incorporation of these precursors into genomic DNA during the S phase of the cell cycle (replication) is detected (Ruefli-Brasse et al., Science 302(5650):1581-4, 2003; Gu et al., Science 302 (5644):445-9, 2003).

In another approach, efficacy is measured by detecting an increase in the number of viable cells present in a tissue or organ relative to the number present in an untreated control tissue or organ, or the number present prior to treatment. Assays for measuring cell viability are known in the art, and are described, for example, by Crouch et al. (J. Immunol. Meth. 160, 81-8); Kangas et al. (Med. Biol.62, 338-43, 1984); Lundin et al., (Meth. Enzymol. 133, 27-42, 1986); Petty et al. (Comparison of J. Biolum. Chemilum.10, 29-34, .1995); and Cree et al. (AntiCancer Drugs 6: 398-404, 1995). Cell viability can be assayed using a variety of methods, including MTT (3-(4,5-dimethylthiazolyl)-2,5-diphenyltetrazolium bromide) (Barltrop, Bioorg. & Med. Chem. Lett.1: 611, 1991; Cory et al., Cancer Comm. 3, 207-12, 1991; Paull J. Heterocyclic Chem. 25, 911, 1988). Assays for cell viability are also available commercially. These assays include but are not limited to CELLTITER-GLO® Luminescent Cell Viability Assay (Promega), which uses luciferase technology to detect ATP and quantify the health or number of cells in culture, and the CellTiter-Glo® Luminescent Cell Viability Assay, which is a lactate dehyrodgenase (LDH) cytotoxicity assay (Promega).

Alternatively, or in addition, therapeutic efficacy is assessed by measuring a reduction in apoptosis. Apoptotic cells are characterized by characteristic morphological changes, including chromatin condensation, cell shrinkage and membrane blebbing, which can be clearly observed using light microscopy. The biochemical features of apoptosis include DNA fragmentation, protein cleavage at specific locations, increased mitochondrial membrane permeability, and the appearance of phosphatidylserine on the cell membrane surface. Assays for apoptosis are known in the art. Exemplary assays include TUNEL (Terminal deoxynucleotidyl Transferase Biotin-dUTP Nick End Labeling) assays, caspase activity (specifically caspase-3) assays, and assays for fas-ligand and annexin V. Commercially available products for detecting apoptosis include, for example, Apo-ONE® Homogeneous Caspase-3/7 Assay, FragEL TUNEL kit (ONCOGENE RESEARCH PRODUCTS, San Diego, Calif.), the ApoBrdU DNA Fragmentation Assay (BIOVISION, Mountain View, Calif.), and the Quick Apoptotic DNA Ladder Detection Kit (BIOVISION, Mountain View, Calif.).

Methods for Evaluating Cardiac Function

Compositions of the invention may be used to enhance cardiac function in a subject having reduced cardiac function. Methods for measuring the biological function of the heart (e.g., contractile function) are standard in the art and are described, for example, in the Textbook of Medical Physiology, Tenth edition, (Guyton et al., W.B. Saunders Co., 2000). In the invention, cardiac function is increased by at least 5%, 10%, 15%, 20%, 30%, 40%, 50%, 60%, 70%, 80%, 90%, or even 100% relative to the cardiac function present in a naturally-occurring, corresponding tissue or organ. Most advantageously, cardiac function is enhanced or damage is reversed, such that the function is substantially normal (e.g., 85%, 90%, 95%, or 100% of the cardiac function of a healthy control subject). Reduced cardiac function may result from conditions such as cardiac hypertrophy, reduced systolic function, reduced diastolic function, maladaptive hypertrophy, heart failure with preserved systolic function, diastolic heart failure, hypertensive heart disease, aortic and mitral valve disease, pulmonary valve disease, hypertrophic cardiomyopathy (e.g., hypertrophic cardiomyopathy originating from a genetic or a secondary cause), post ischemic and post-infarction cardiac remodeling and cardiac failure.

Any number of standard methods are available for assaying cardiovascular function. Preferably, cardiovascular function in a subject (e.g., a human) is assessed using non-invasive means, such as measuring net cardiac ejection (ejection fraction, fractional shortening, and ventricular end-systolic volume) by an imaging method such echocardiography, nuclear or radiocontrast ventriculography, or magnetic resonance imaging, and systolic tissue velocity as measured by tissue Doppler imaging. Systolic contractility can also be measured non-invasively using blood pressure measurements combined with assessment of heart outflow (to assess power), or with volumes (to assess peak muscle stiffening). Measures of cardiovascular diastolic function include ventricular compliance, which is typically measured by the simultaneous measurement of pressure and volume, early diastolic left ventricular filling rate and relaxation rate (can be assessed from echoDoppler measurements). Other measures of cardiac function include myocardial contractility, resting stroke volume, resting heart rate, resting cardiac index (cardiac output per unit of time [L/minute], measured while seated and divided by body surface area [$m^2$])) total aerobic capacity, cardiovascular performance during exercise, peak exercise capacity, peak oxygen ($O_2$) consumption, or by any other method known in the art or described herein. Measures of vascular function include determination of total ventricular afterload, which depends on a number of factors, including peripheral vascular resistance, aortic impedance, arterial compliance, wave reflections, and aortic pulse wave velocity, Methods for assaying cardiovascular function include any one or more of the following: Doppler echocardiography, 2-dimensional echo-Doppler imaging, pulse-wave Doppler, continuous wave Doppler, oscillometric arm cuff, tissue Doppler imaging, cardiac catheterization, magnetic resonance imaging, positron emission tomography, chest X-ray, X ray contrast ventriculography, nuclear imaging ventriculography, computed tomography imaging, rapid spiral computerized tomographic imaging, 3-D echocardiography, invasive cardiac pressures, invasive cardiac cardiac flows, invasive cardiac pressure-volume loops (conductance catheter), non-invasive cardiac pressure-volume loops.

Kits

Compositions comprising a cell of the invention (e.g., a cardiac or mesenchymal stem/progenitor cell that expresses or is primed with CTGF, insulin, or IGF-1) or a composition comprising biologically active agents (e.g., CTGF, insulin, or IGF-1) is supplied along with additional reagents in a kit. The kits can include instructions for the treatment regime, reagents, equipment (test tubes, reaction vessels, needles, syringes, etc.) and standards for calibrating or conducting the treatment. The instructions provided in a kit according to the invention may be directed to suitable operational parameters in the form of a label or a separate insert. Optionally, the kit may further comprise a standard or control information so that the test sample can be compared with the control information standard to determine if whether a consistent result is achieved.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Conditioned Medium From Human Stromal Cells Induced Rat CPC Proliferation

Figure 2A:
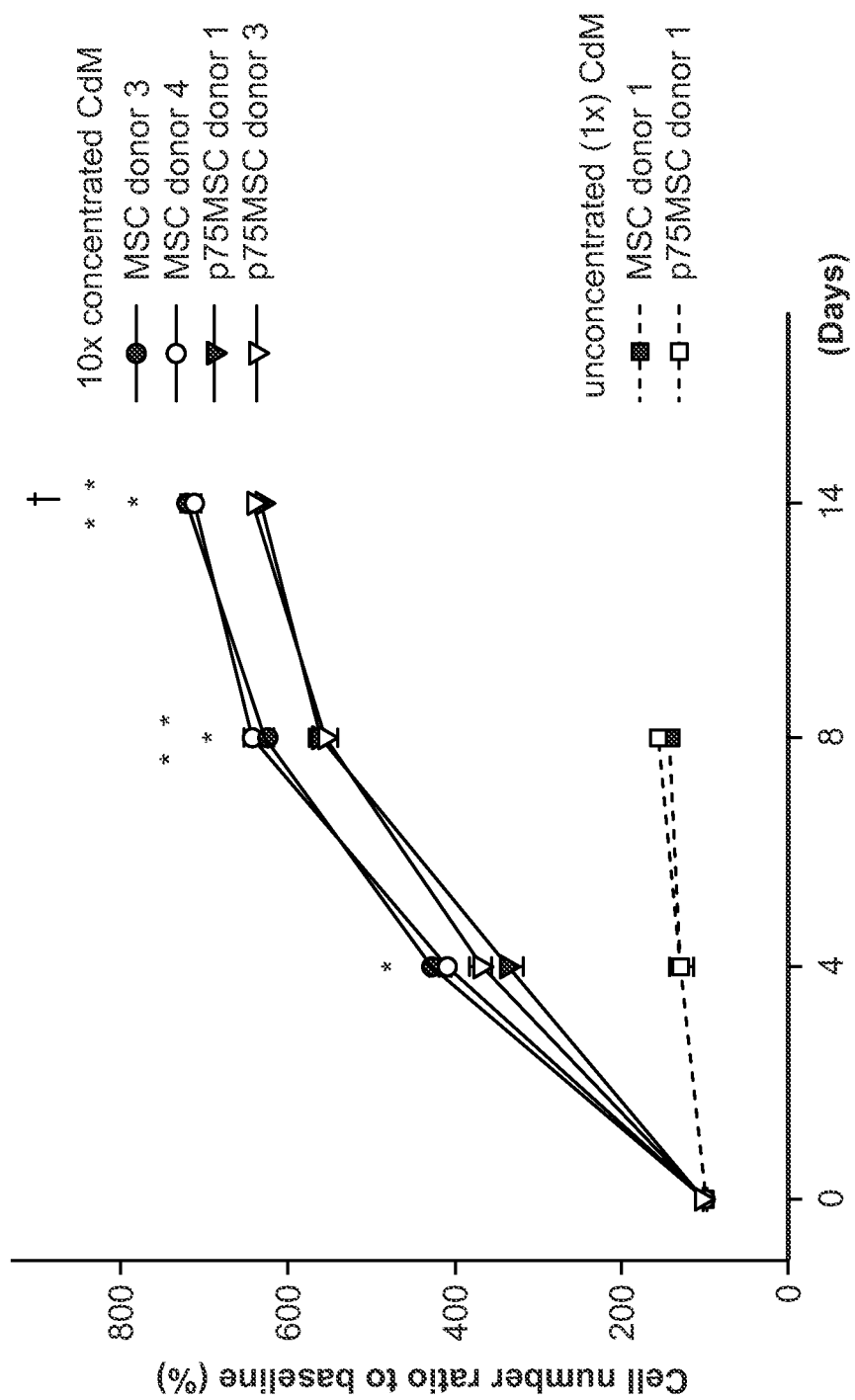
FIGS. 2A-2C depict proliferation of CPCs.

Conditioned medium (CdM) was collected from human mesenchymal stem cells (MSCs), p75MSCs, and dermal fibroblasts. CdM from each of the cell types supported CPC proliferation (FIG. 1A). In contrast, the number of CPCs incubated in CdM vehicle (serum-free α-MEM (SFM)) gradually decreased (FIGS. 1A and 1B). A concentration-dependent increase in CPC number was observed when CPCs were incubated in 10×-concentrated CdM (10× CdM) from MSCs or p75MSCs (FIG. 2A). To confirm DNA synthesis and active cell cycle status, incorporation of BrdU into CPCs was quantified 24 hrs after exposure to CdM. The percentage of BrdU-positive CPCs in CdM from MSCs, p75MSCs or fibroblasts was significantly greater than that for SFM-treated CPCs (FIG. 1B). Immunoblotting demonstrated that Ki67 was expressed in CPCs treated with CdM but not in CPCs treated with serum free medium (FIG. 1B). In contrast to its effects on CPCs, CdM from MSCs or p75MSCs did not support the proliferation of adult rat cardiac fibroblasts (FIG. 1C).

Example 2

CdM From Human MSCs Activated STAT3 and Akt in CPCs

Figure 3A:
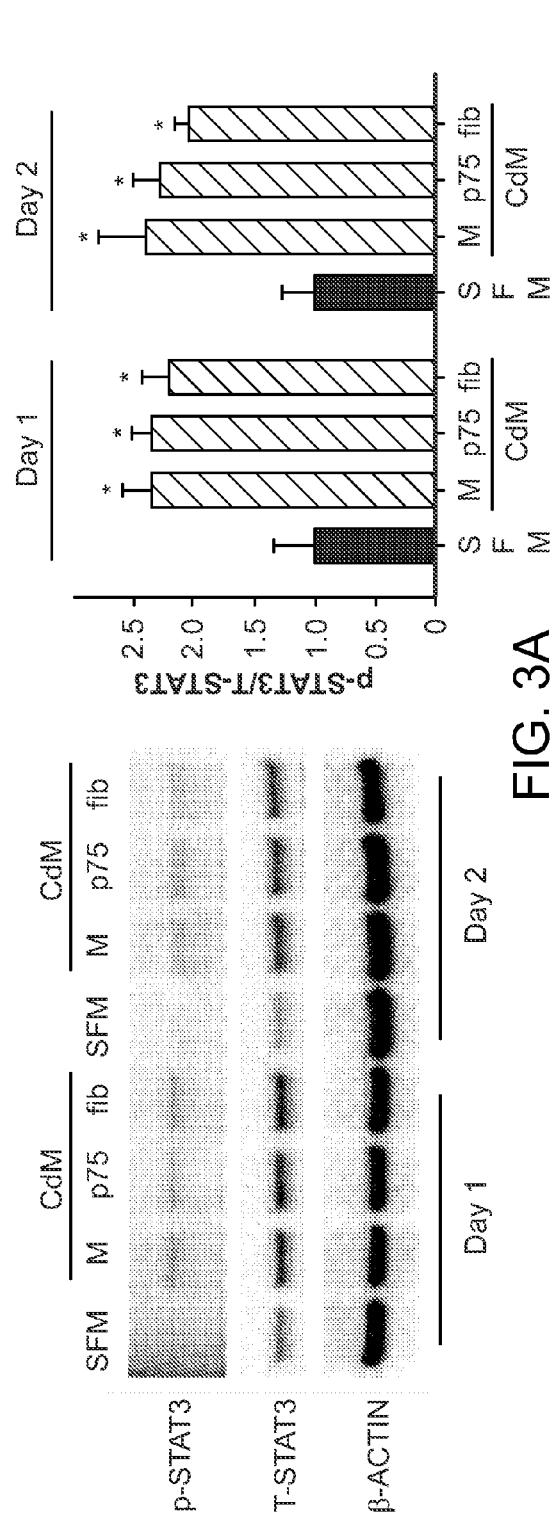
FIGS. 3A-3E depict STAT3 and Akt activation in CPCs treated with 1× CdM.
Figure 3C:
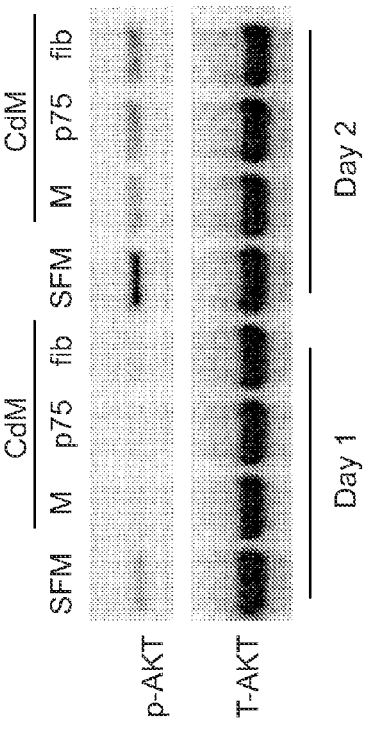
Figure 3B:
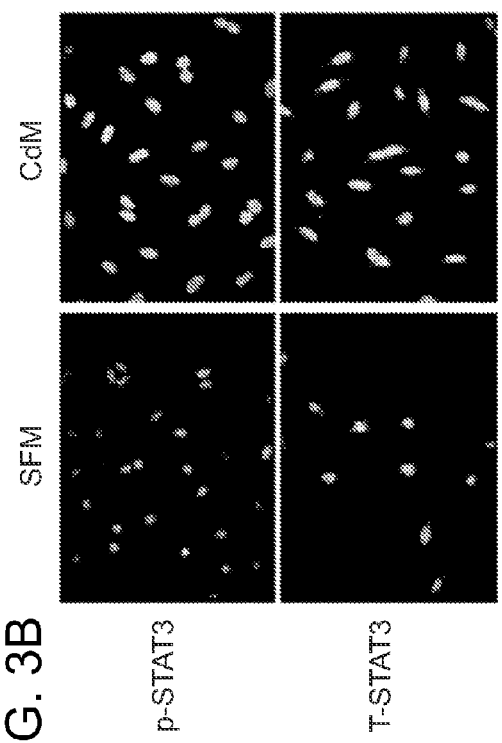

STAT3 activation is important for the self-renewal of ES cells, adult HSCs, and adult neural stem cells. Accordingly, levels of phosphorylated-STAT3 (p-STAT3) in CPCs exposed to CdMs from MSCs, p75MSCs, or fibroblasts were assayed. Levels of p-STAT3 were significantly higher in CPCs at 1 and 2 days after CdM treatment compared with SFM treatment (FIG. 3A). Immunocytochemistry demonstrated that p-STAT3 localized to the nuclei of CPCs treated with CdM (FIG. 3B). In addition to p-STAT3, phosphorylation of Akt (p-Akt) was observed after incubation of CPCs in CdM from each of the stromal cell types (FIG. 3C). However, p-Akt in CPCs incubated in SFM alone was also observed (FIG. 3C). Notably, auto-phosphorylation of signaling molecules affecting cell survival, such as Akt, ERK1/2, and mTOR occurs in diverse cell types during serum or nutrient deprivation.

Figure 2B:
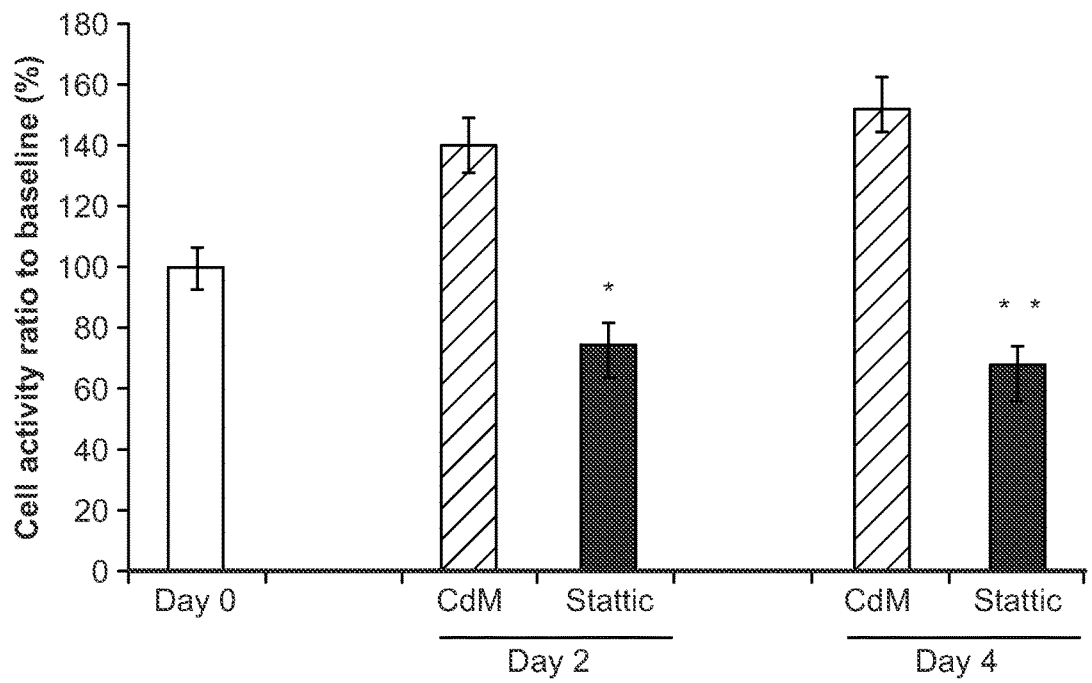
Figure 3E:
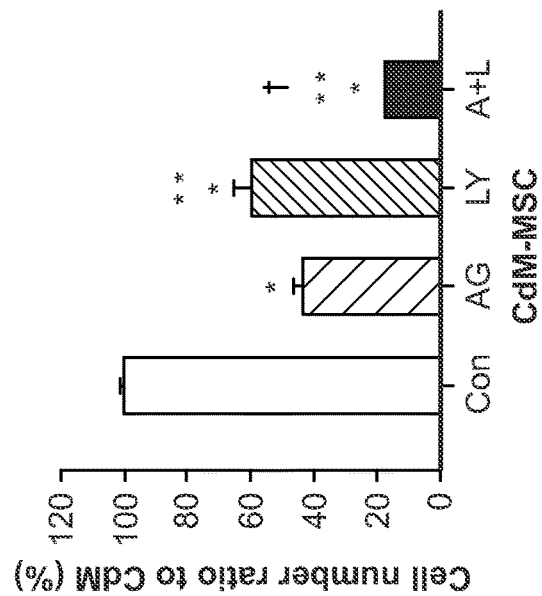
Figure 3D:
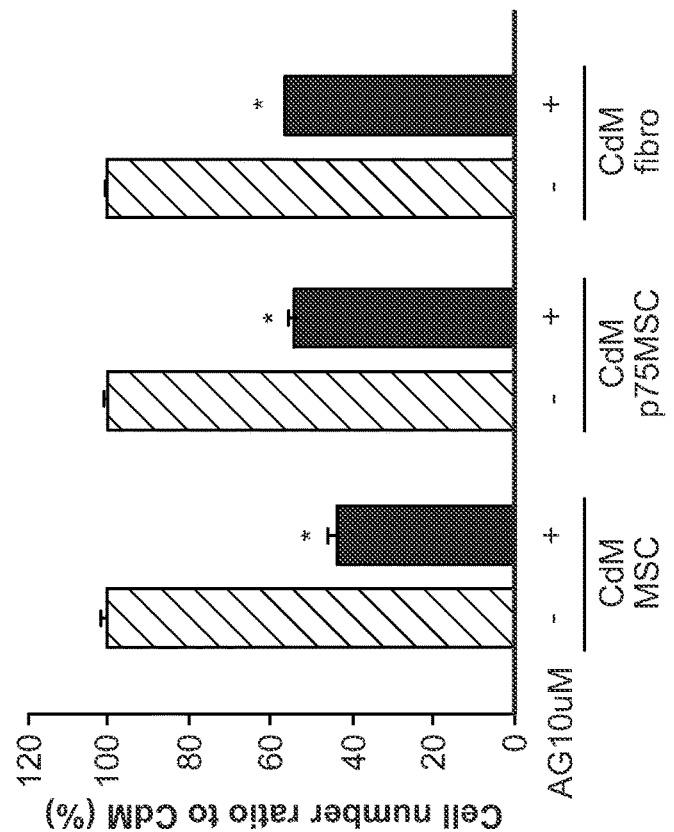

To determine whether p-STAT3 and/or p-Akt mediated the effects of CdM on CPCs, CPCs were treated with pharmacological inhibitors. AG490, a Jak2/STAT3 pathway inhibitor, reduced the number of CPCs treated with MSC CdM in a dose-dependent manner: control (CdM+DMSO), 100±1.5%; 1 μM, 96.3±0.9%; 5 μM, 89.5±0.9%; 10 μM, 43.4±2.4% (cell number ratio to control cell number [121, 863 cells], mean±SEM, n=3 to 6). The inhibitory effect of AG490 (10 μM) was also observed for CPCs treated with CdM from p75MSCs or fibroblasts (FIG. 3D). LY294002, a phosphatidylinositol 3-kinase (PI3K)/Akt pathway inhibitor (10 μM), decreased CPC number in CdM, but to a lesser extent than AG490 (FIG. 2E). Combined treatment with AG490 and LY294002 (10 μM, each) was most effective in reducing CPC number in CdM (FIG. 3E). Incubation of CPCs in "Stattic" (10 μM), a highly specific STAT3 inhibitor (Schust et al., Chem Biol 2006; 13(11):1235-1242), confirmed the role of STAT3 activation in CdM-mediated effects on CPC proliferation (FIG. 2B). PD98059, an ERK inhibitor, did not diminish CPC proliferation in CdM.

Figure 2C:
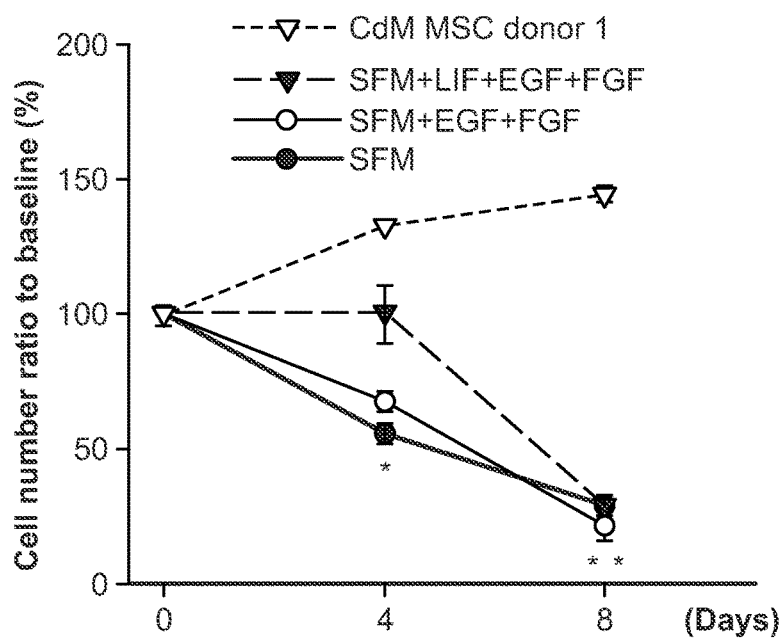

Insulin and Insulin-like growth factor 1 (IGF-1) bind to tyrosine kinase holoreceptors and promote cell survival and proliferation by signaling through the PI3K/Akt and Ras/MAP kinase pathways. Partial functional redundancy for Insulin and IGF-1 signaling is evidenced by signaling through receptor heterodimers IR/IGF-1R and bidirectional cross-talk between ligands/receptors. CSCs/CPCs did not proliferate in the absence of medium supplements containing Insulin (e.g. Insulin-Transferrin-Selenium [ITS] or fetal calf serum), even when in the presence of other mitogenic components from CSC/CPC growth medium such as LIF, EGF or bFGF (FIG. 2C). This suggested that CdM from human stromal cells may contain Insulin, IGF-1, or both.

Example 3

CdM Protected CPCs Exposed to Hypoxia

Figure 4A:
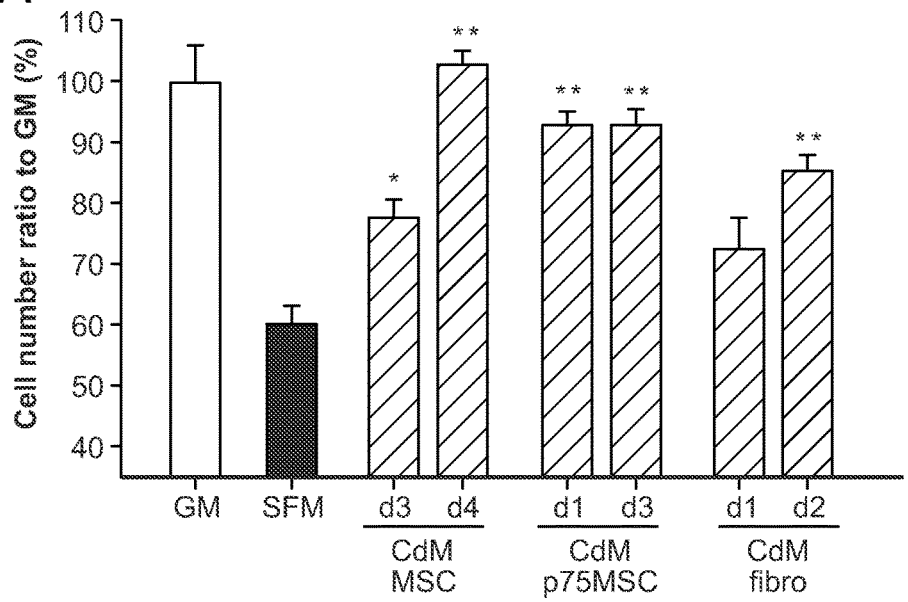
FIGS. 4A-4C depict the protective effect of human stromal cell CdM on rat CPCs exposed to chronic hypoxia (1% oxygen for 48 hrs).
Figure 4B:
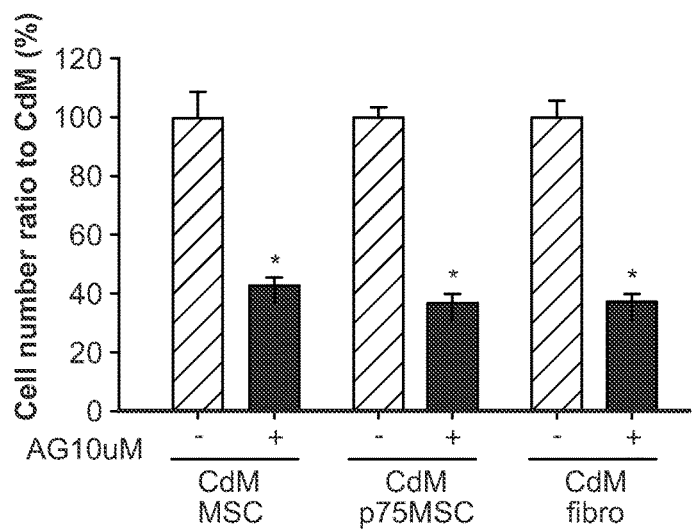
Figure 4C:
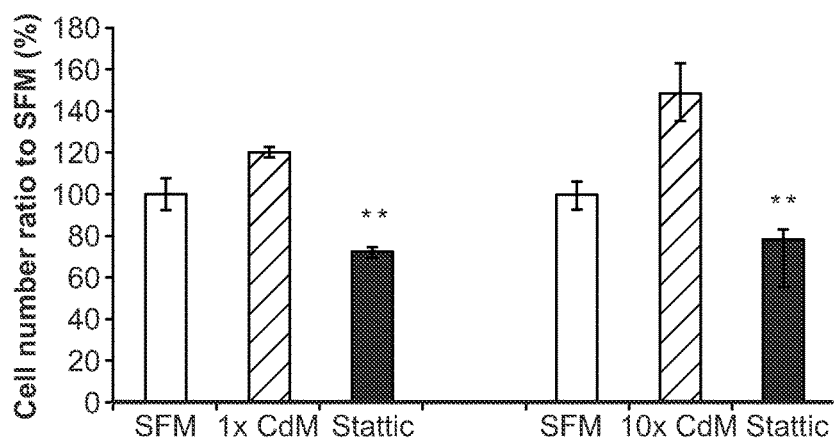

Because cells transplanted to the heart after myocardial infarction (MI) may encounter hypoxic environments, it was examined whether CdM could protect CPCs during exposure to 1% oxygen for 48 hrs ex vivo. CdM from MSCs and p75MSCs significantly promoted the survival of CPCs compared with SFM (FIG. 4A). Compared with cell survival in CPC growth medium (positive control; 100±6.2%), survival of CPCs in SFM was 59.9±3.2% while that of CPCs incubated in MSC CdM was 90.3±6.0% (P<0.05 vs SFM) and p75MSCs CdM was 93±1.5% (P<0.0001 vs SFM). Survival of CPCs incubated in 1× CdM from 1 of 2 MSC donors tested and both p75MSC donors tested was not significantly different from that in growth medium (MSC donor 4, P=0.66; p75MSC donor 1, P=0.33; p75MSC donor 3, P=0.37). Addition of STAT3 inhibitor abolished CdM-mediated protection of CPCs under hypoxic conditions (AG490, FIG. 4B; Stattic, FIG. 4C).

Example 4

CPCs Incubated in CdM Retained Their Multipotent Differentiation Capacity

Figure 5:
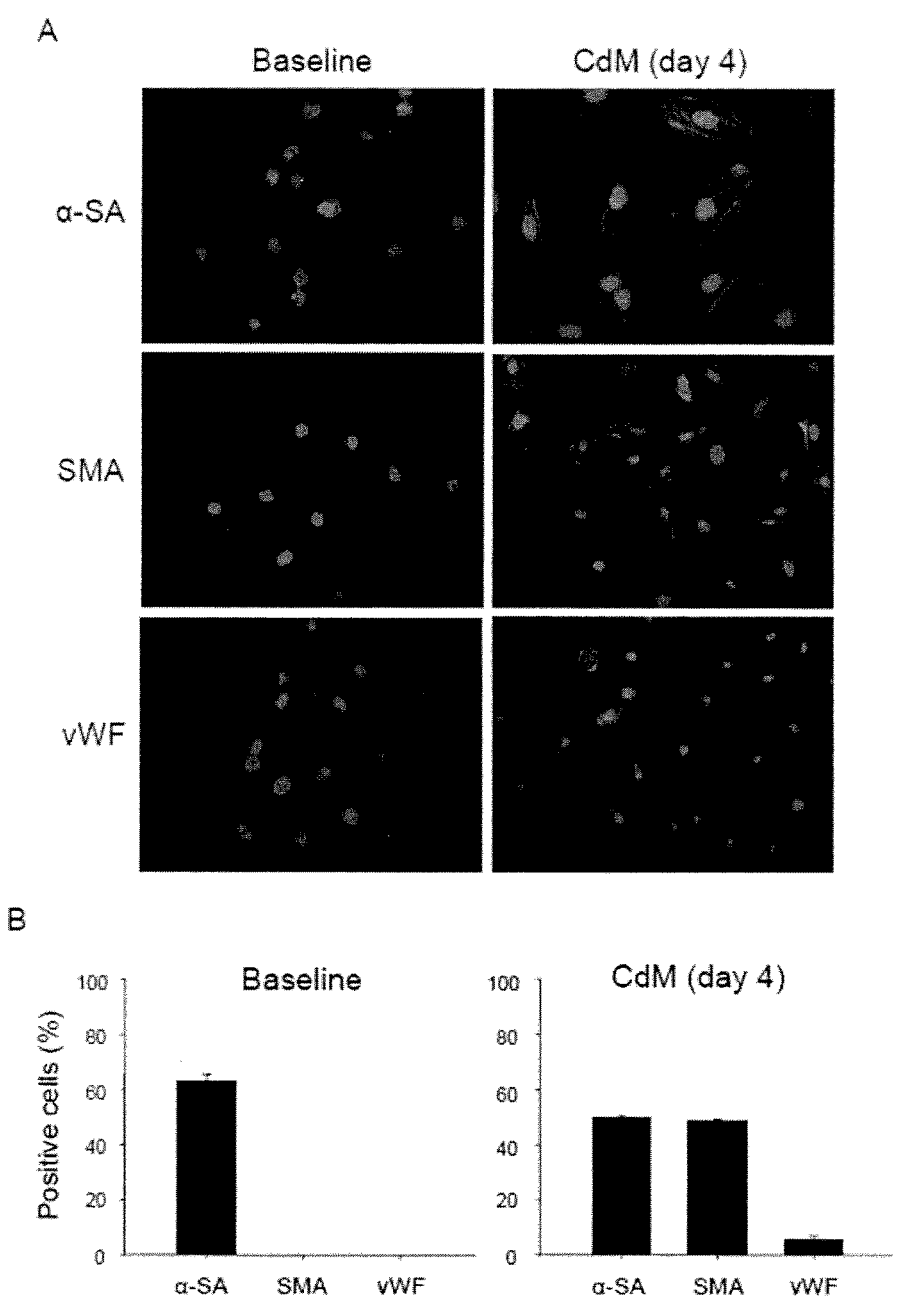
FIGS. 5A and 5B depict differentiation of CPCs expanded in CdM.

Control CPCs cultured in CPC growth medium were negative for α-smooth muscle actin and von Willebrand Factor staining, whereas about 60% expressed α-sarcomeric actin (FIGS. 5A and 5B, left). In contrast, clones of CPCs exposed to 1× CdM for 4 days stained positively for α-sarcomeric actin, α-smooth muscle actin, and von Willebrand Factor (FIGS. 5A and 5B, right). After 4 days in CdM, CPC-derived cells no longer expressed the CSC antigen, c-Kit, indicating progress toward differentiation.

Example 5

Intra-Arterial Infusion of p75MSC CdM Improved Cardiac Function After MI

Figure 6:
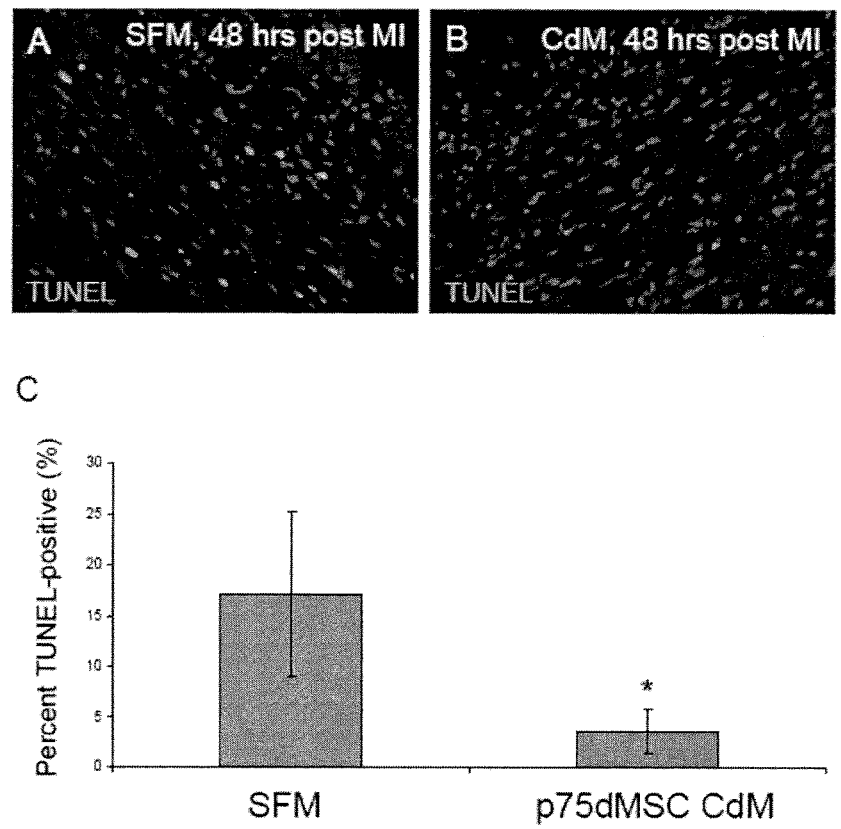
FIG. 6 depicts intra-arterial infusion of p75MSC CdM significantly reduced cardiac apoptosis/necrosis 48 hrs after MI.
Figure 7:
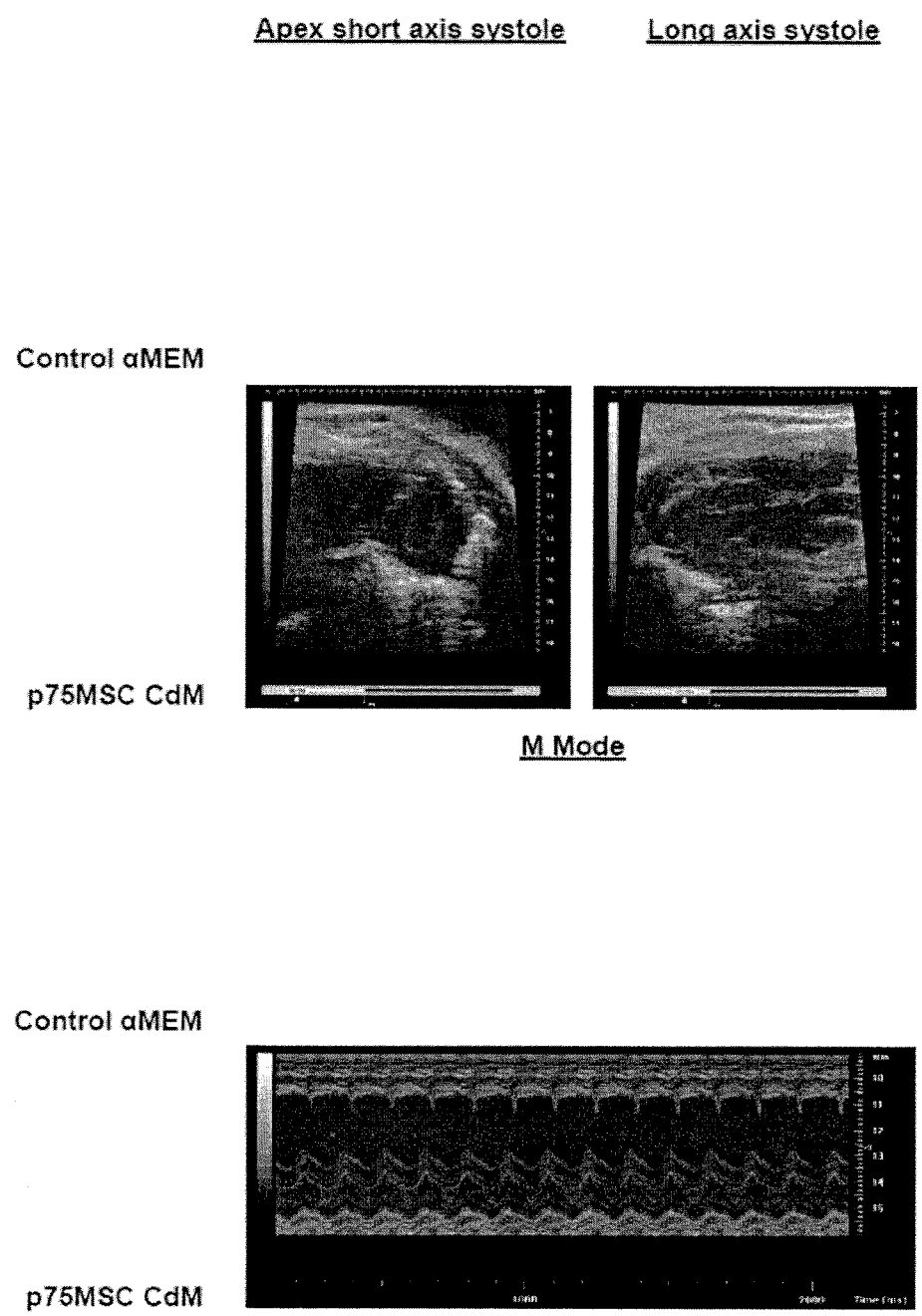
FIG. 7 depicts representative images from echocardiography showing intra-arterial infusion of 30× p75MSC CdM 24 hrs after MI improved cardiac function 1 week after MI.

Based on the results with CdM and cultured CPCs, it was examined whether infusion of CdM after MI would increase the number of endogenous CPCs to improve cardiac repair and function. MI was produced in C57bl6/J mice by permanent ligation of the left anterior descending coronary artery (LAD). The following day, mice were randomized to receive treatment with intra-arterial infusion (left ventricle lumen) of 30× p75MSC CdM or vehicle (SFM). Mice from each group were euthanized at 1 day or 1 week after treatment. Hearts obtained 1 day after treatment were sectioned and processed for TUNEL and immunohistochemistry to detect c-Kit. TUNEL assays showed that CdM infusion significantly reduced cardiac apoptosis/necrosis (SFM, 17.2±8.1%; CdM, 3.7±2.2%; P<0.05, FIG. 6). Intra-muscular injection of porcine MSCs from bone marrow, but not their conditioned medium, was reported to increase the number of c-Kit$^+$ cells in the hearts of pigs after MI. After intra-arterial infusion of CdM from human p75MSCs, rare c-Kit$^+$ cells were detected in heart sections from both CdM- and SFM-treated mice. However, because c-Kit$^+$ cell number was variable and did not appear to differ between mice that received CdM or SFM, c-Kit$^+$ cells were not quantified. At 1 week after treatment, echocardiographic measurements demonstrated significantly improved cardiac function in mice that received CdM compared with SFM (FIGS. 7 and 8). Biochemical assays for residual myocardial Creatine Kinase (CK) activity in left ventricular (LV) homogenates indicated that CdM- and SFM-treated mice had similar size infarcts at 1 week after MI (Anterior LV, SFM, 4.66±0.40; CdM, 5.00±0.43, P=0.21; Posterior LV, SFM, 6.59±0.32; CdM, 6.34±0.33, data expressed as IU CK/mg protein, mean±SD, P=0.23; SFM, n=6; CdM, n=5).

Example 6

Priming of CSCs With CdM From p75MSCs Improved Graft Success After MI

Figure 9:
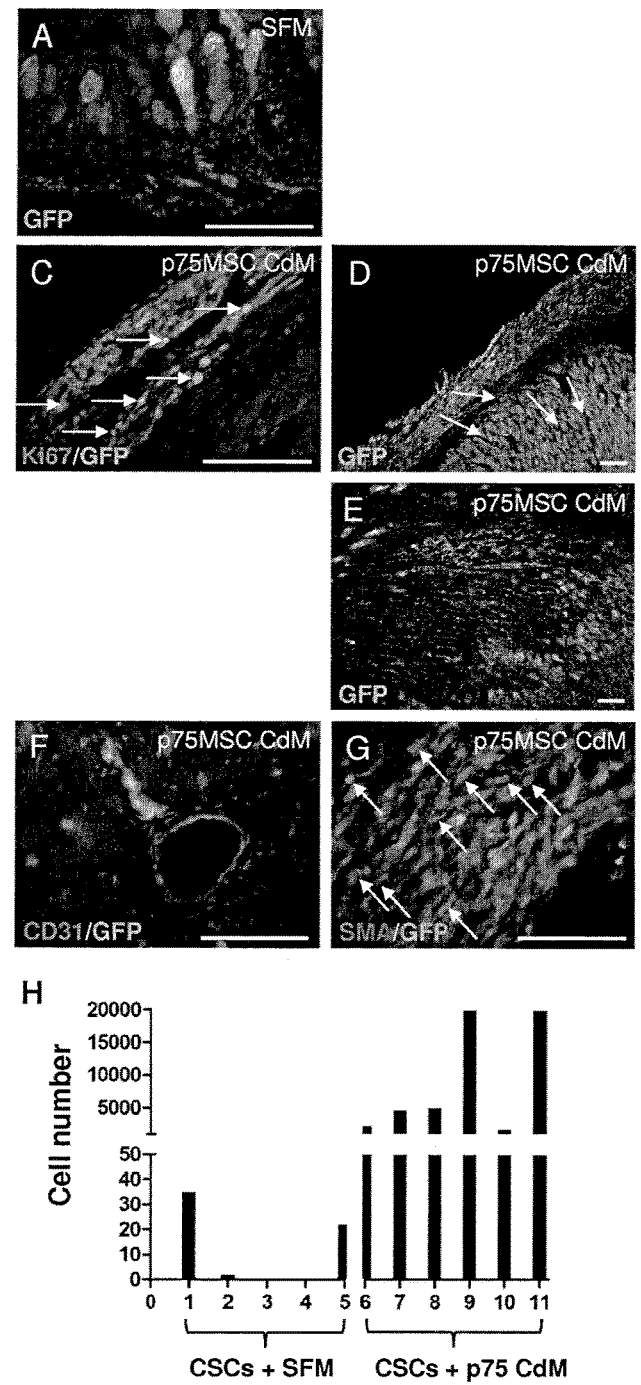
FIGS. 9A-9H show that priming of adult rat CSCs with human p75MSC CdM markedly improved CSC graft success 1 week after MI. At 1 day after MI, CSCs were primed in 30× CdM or vehicle (SFM) for 30 min. on ice prior to co-injection (2 sub-epicardial injections per rat, 1 per border zone).
Figure 10:
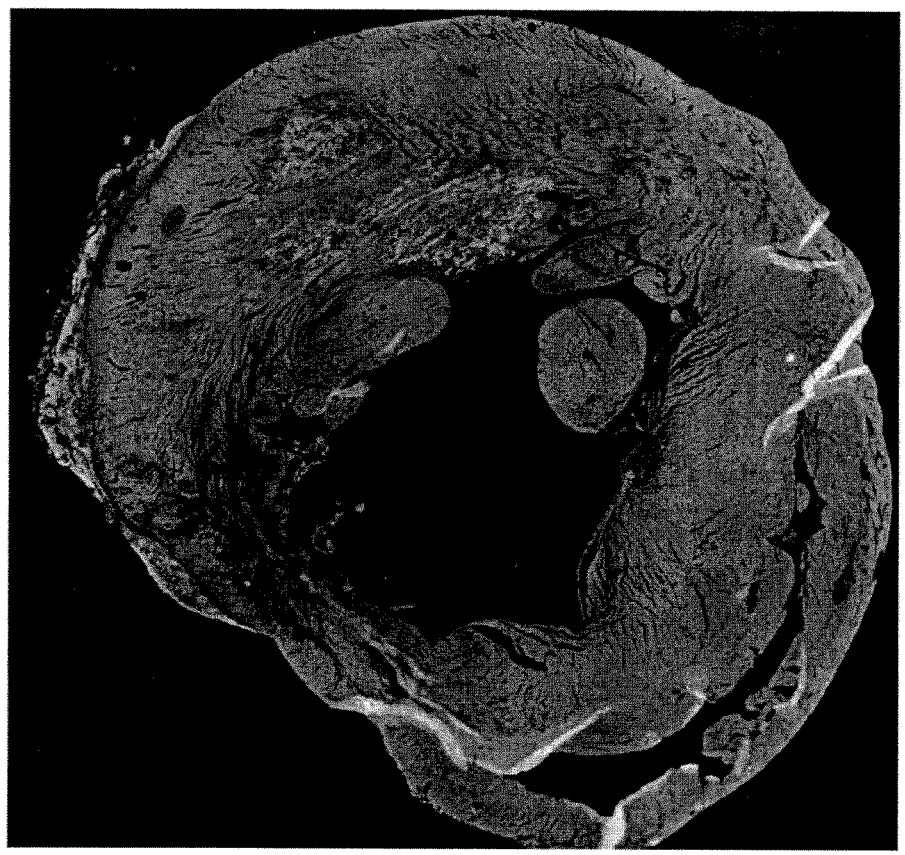
FIG. 10 is an image showing the localization of CSC-derived GFP$^+$ cells, 1 week after MI and CSC/CdM injections. CSCs primed with 30× p75MSC CdM engrafted into sub-epicardial tissues after MI and migrated into specific zones with infarction. Magnification, 200×.

Based on the observations with p75MSC CdM and its ability to increase proliferation and survival of cultured CSCs/CPCs, it was determined whether prior exposure of CSCs to p75MSC CdM could foster the grafting of CSCs to the injured heart. MI was produced in Fischer rats by permanent ligation of the LAD. One day after MI, syngeneic GFP-positive rat CSCs were primed for 30 min. on ice in p75MSC CdM (30× CdM, n=6 rats) or vehicle (SFM, n=5 rats). The chest wall was re-opened and rats were randomized to treatment with co-injections of CSCs/CdM or CSCs/SFM (125,000 cells/5 μl injection, 2 sub-epicardial injections, 1 per border zone). At 1 week after MI, rats were euthanized and their hearts were processed as frozen serial-sections from apex to base. For each heart, GFP$^+$ cells were quantified in the tissue section with the most GFP$^+$ cells. For 2 rats in CSCs/SFM co-injection group, GFP$^+$ cells were not detected. Furthermore, hearts from CSC/SFM rats with the highest level of engraftment contained less than 40 GFP$^+$ cells/section (FIG. 9A). In contrast, many sections from rats co-injected with CSCs/CdM contained several thousand GFP$^+$ cells (FIG. 9B-9E). After priming of CSCs in p75MSC CdM, GFP$^+$ cells grafted into sub-epicardial locations, proliferated (see Ki67 stain, FIG. 4B), and migrated into zones with infarction (FIGS. 9C-9G and 10). Furthermore, after 1 week, derivatives from CSCs primed in CdM engrafted into blood vessel walls as CD31-positive endothelial cells (FIG. 9F). They also generated smooth muscle cells and myofibroblasts (smooth muscle alpha actin-positive, FIG. 9G). Although they grafted into sub-epicardial locations after MI, GFP$^+$ cells derived from vehicle-primed CSCs did not stain for Ki67, and had not entered myocardial tissue from sub-epicardial tissue at 1 week after MI and treatment (FIG. 9A).

Example 7

CdM Contains Human CTGF and Insulin That Activated CSCs/CPCs

Figure 11A:
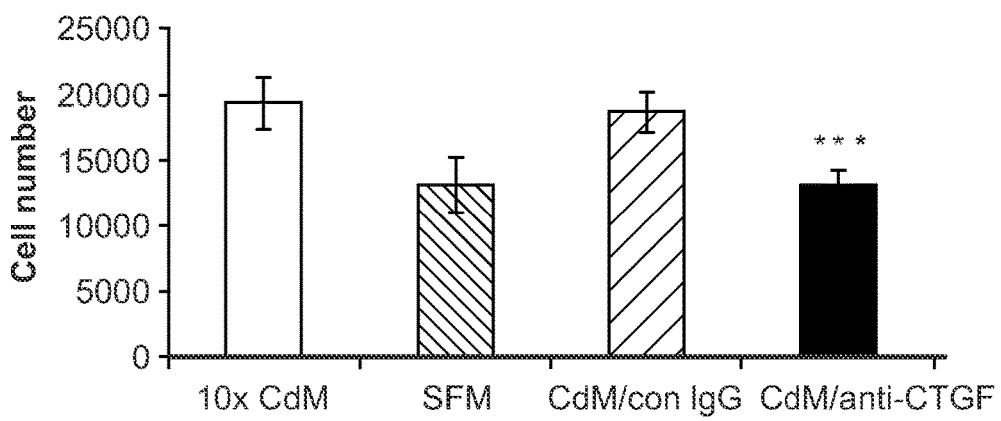
Figure 11B:
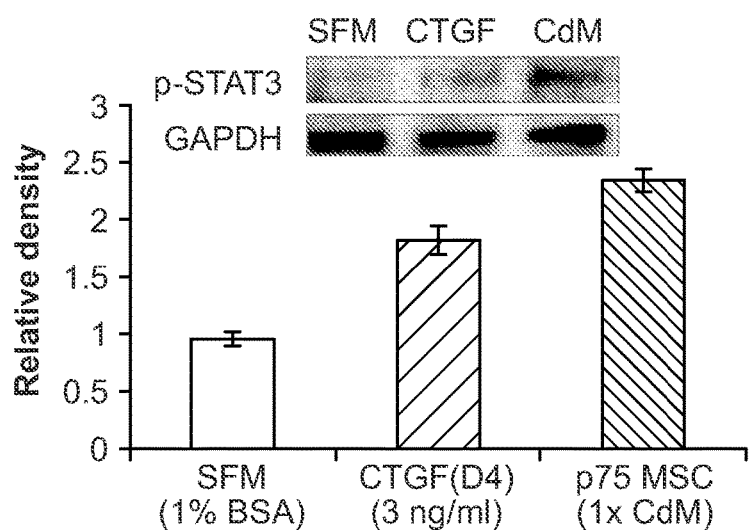

To identify factors in p75MSC CdM that promoted the proliferation and survival of CPCs, Affymetrix gene expression profiles were examined from human p75MSCs that were freshly sorted from marrow aspirates and from p75MSCs cultured adherently for 2 passages (Bakondi et al., Mol Ther 2009; 17(11):1938-1947). Antibody blocking/neutralization studies for selected secreted factors were carried out with 10× p75MSC CdM and CPCs exposed to hypoxic conditions (1% oxygen, 48 hrs). Under hypoxia, neutralizing antisera specific to human CTGF prevented CdM from protecting CPCs (P<0.001, FIG. 11A). Of interest, addition of human CTGF alone to SFM containing 1% BSA significantly induced p-STAT3 in CPCs (see inset, FIG. 11A). By ELISA, 10× p75MSC CdM contained 1.00±0.02 ng/ml human CTGF. Although human IGF-1 in p75MSC CdM was not detected, it was found that 10× p75MSC CdM contained 8.75±2.7 ng/ml of bovine Insulin. Furthermore, neutralizing antibodies specific to Insulin significantly reduced CdM-mediated protection of CPCs during hypoxia exposure, albeit not as much as did blocking CTGF (MTS assay[$Abs^{490}$]: non-specific IgG, 0.378±0.021; anti-Insulin, 0.270±0.034; mean±SD, n=4, P<0.05). Addition of recombinant human Insulin to CPCs induced p-Akt in a dose-responsive manner and increased also CPC survival and proliferation under hypoxic conditions (FIG. 11B). Notably, CPC protection assays with human Insulin or IGF-1 alone (30 ng/ml, each) demonstrated that they were equivalent in their ability to rescue CPCs exposed to hypoxia (control [SFM with 1% BSA]: 9004±12 cells; Insulin: 13,507±1,473 cells; IGF-1, 14,894±559 cells; mean±SD, n=3, P=0.24).

Figure 11C:
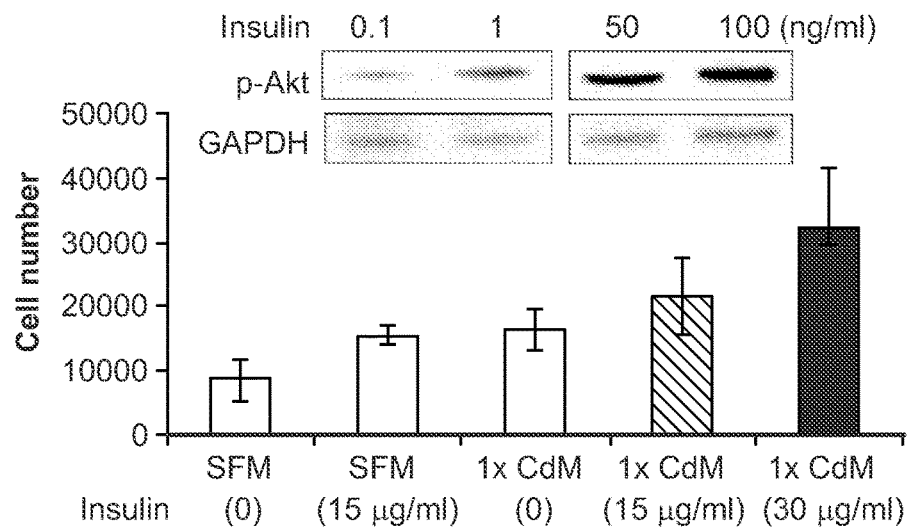
Figure 11D:
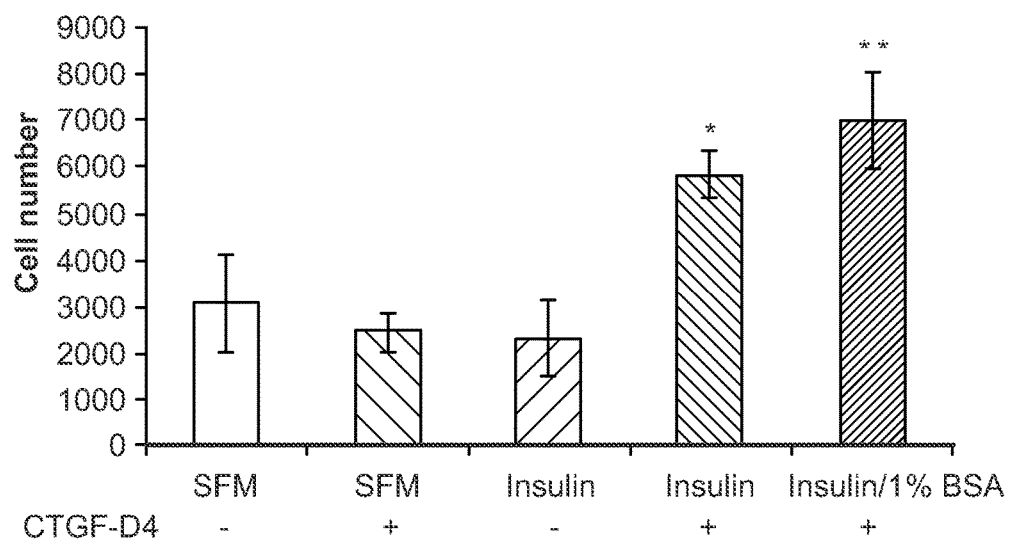

CTGF (CCN2, IGFBP8) consists of 4 domains and the C-terminal (4th) domain alone was reported to increase cell adhesion and proliferation (Steffen et al., Growth Factors. 1998; 15(3):199-213; Gao et al. J Biol Chem. 2004; 279(10): 8848-8855.). In experiments with recombinant peptides, combined treatment with human C-terminal CTGF peptide (CTGF-D4) and Insulin (i.e., alpha chain-beta chain dimer) had synergistic effects on CPC survival and proliferation under hypoxic conditions. For example, CTGF-D4 or Insulin alone (1 ng/ml in SFM, each) did not protect CPCs against 48 hr of hypoxia (FIG. 11C). In contrast, addition of both CTGF-D4 and Insulin to SFM (1 ng/ml, each) provided significant protection of CPCs against hypoxia (P<0.05, FIG. 11C). CTGF-D4/Insulin-mediated protection of CPCs was enhanced by including 1% BSA as a carrier (P<0.01, FIG. 1C)

Example 8

A Defined Combination of CTGF-D4/Insulin Promoted CSC Grafts After MI

Figure 12:
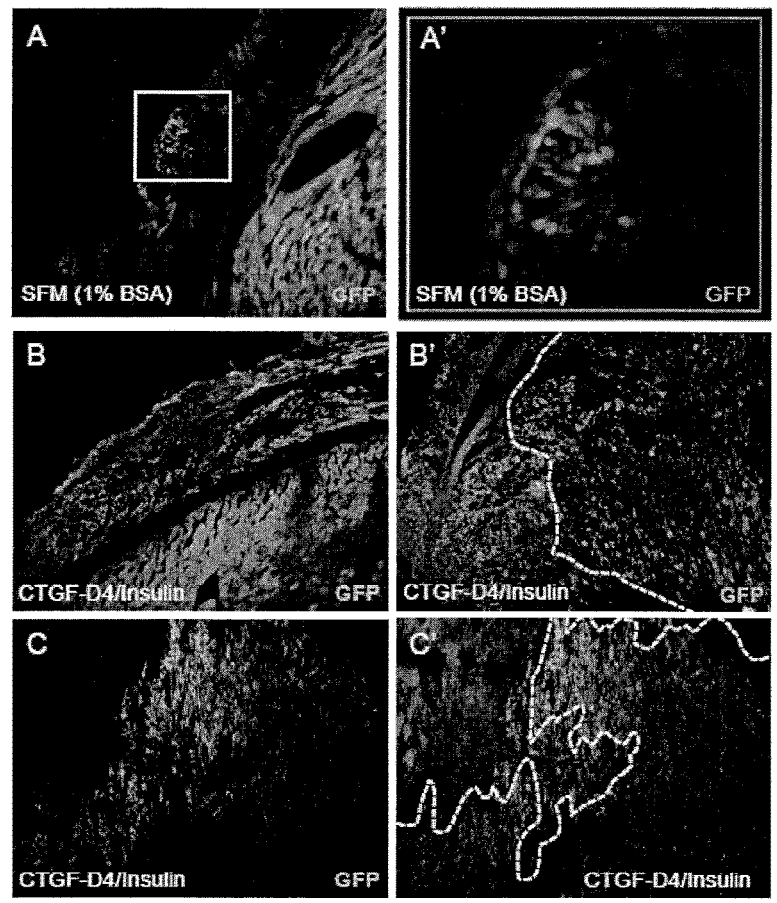

Having observed synergistic protective effects after CTGF-D4/Insulin treatment of cultured CPCs exposed to simulated ischemia (FIG. 11C), it was hypothesized that a priming mixture based on the CTGF-D4/Insulin ratio found in 30× p75MSC CdM would promote CSC engraftment when using to prime CSCs. One day after MI, GFP CSCs were incubated on ice with SFM containing 1% BSA, CTGF-D4 (3 ng/ml), and Insulin (30 ng/ml), or with vehicle (SFM with 1% BSA) for 30 min. prior to co-injection into border zone areas of rats randomized to treatment (125,000 cells/5 μl injection, 2 sub-epicardial injections, 1 per border zone). As before, all rats were euthanized 1 week after MI and their hearts were processed as serial sections. Whereas few rats that received co-injections of CSCs/vehicle had detectable GFP$^+$ cells after 1 week (n=1/7 rats, FIGS. 12A and 12B), all rats that received CSCs/CTGF-D4/Insulin exhibited a level of engraftment consistent with results obtained by priming with 30× p75MSC CdM (5/5 rats, FIG. 12B-12C'). Similar to CSCs primed in CdM, CSCs primed in CTGF-D4/Insulin grafted into sub-epicardial locations, proliferated, and provided GFP$^+$ CSC derivatives that migrated into host myocardium, reaching areas of infarction with few remaining viable myocytes (FIG. 12B'-12C').

Example 9 p75-CdM and CTGF-D4 Promoted Signaling Through the Wnt Pathway in Epicardial-Derived Cells (EPDC)

Figure 13:
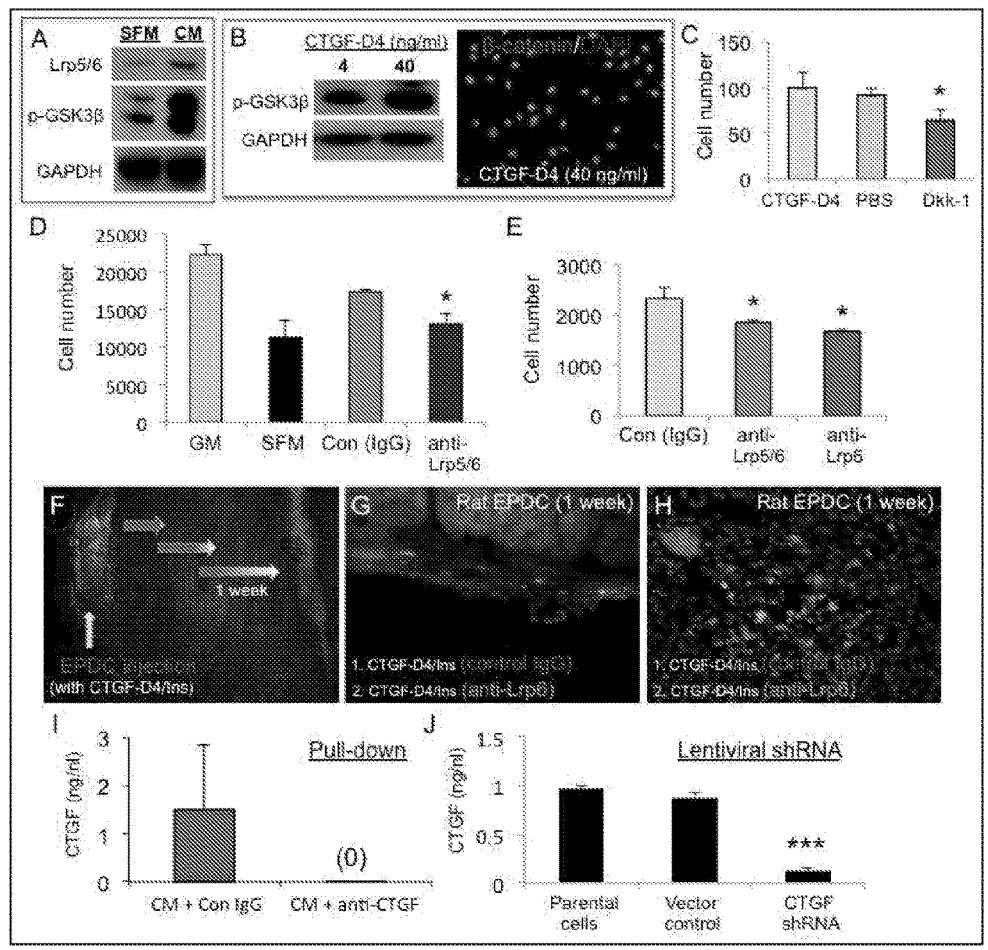
FIGS. 13A-13J show involvement of the Wnt pathway in the effects of p75-CdM and CTGF-D4 on epicardial-derived cells.

While examining different signaling pathways that might be stimulated by p75-CdM and/or CTGF-D4, it was found that epicardial-derived cells (EPDC) expressed the Wnt co-receptor Lrp5/6 and that both p75-CdM and CTGF-D4 promoted signaling through the canonical Wnt pathway, as evidenced by phosphorylation of GSK3β and accumulation of nuclear β-catenin (FIGS. 13A and 13B). Wnt signaling occurs when a Wnt ligand associates with Frizzled (FRZ) and Lrp5/6, a Wnt ligand co-receptor. This results in activation of the cytoplasmic phosphoprotein, Disheveled (DSH) and release of β-catenin from a "destruction complex" made up of the scaffold protein, Axin, the tumor suppressor protein adenomatous polyposis coli (APC), and glycogen synthase kinase 30 (GSK3β). Under these conditions, GSK3β does not phosphorylate β-catenin; this leads to accumulation of β-catenin in the cell nucleus where it binds to TCF/LEF family transcription factors and activates gene transcription. In the absence of Wnt ligand or receptor stimulation, β-catenin is phosphorylated by GSK3β, tagged by an E3 ubiquitin ligase, and destroyed by proteasomal degradation.

Furthermore, incubation of EPDCs in Dkk-1, a secreted inhibitor of Lrp6, significantly reduced the protection normally conferred by CTGF-D4 when EPDCs were incubated under hypoxic conditions (1% oxygen, 48 hr)(p<0.05, FIG. 13C). To determine whether CTGF-D4 interacted with Lrp6 to promote EPDC survival, cell protection assays were performed under hypoxia and with neutralizing antisera to LrpS/6 or specifically, Lrp6. Both antibodies significantly reduced the protection conferred by CTGF-D4 (p<0.05 for both, FIGS. 13D and 13E).

It was also investigated whether signaling through CTGF-D4/Lrp6 played a role in graft success after MI. A two-color competitive grafting assay for EPDCs was developed to be able to evaluate inhibition effects (e.g. primed with CTGF-D4 and anti-Lrp6) on a separate aliquot of cells from the same isolate that was used for control (e.g. primed with CTGF-D4/Insulin and non-specific IgG). Importantly, labeling of EPDCs with cell-tracking dye did not affect their ability to graft and migrate into the heart after MI (see distance traveled from subepicardial injection site at 1 week in FIG. 1F). Adding blocking antisera to Lrp6 to the CTGF-D4/Insulin priming mix substantially reduced the number of grafted EPDCs when hearts were examined at 1 week after MI (cell transplant 1 day after MI)(FIGS. 13G and 13H). The difference for control cells (non-specific IgG, red) and anti-Lrp6 cells (green) was especially evident at locations distal to the subepicardial graft site (FIG. 13H). Pull-down assays were performed to remove CTGF from p75-CdM (FIG. 13I). In addition, lentiviral transductions of human p75MSCs with shRNAs against CTGF were performed. Several different puromycin-selectable CTGF shRNA vectors were tried. One that was not detrimental to p75MSC growth was identified, and elicited a ~60% decrease in CTGF levels by ELISA ($p<0.0001$ compared with CdM from control cells transduced with a scrambled shRNA vector, FIG. 13J).

These results show that the Wnt pathway is involved in the effects of p75-CdM and CTGF-D4 on epicardial-derived cells.

Example 10

CTGF-D4 Promoted Adhesion to Fibronectin and EMT-Like Differentiation in Epicardial-Derived Cells (EPDC)

Figure 14D:
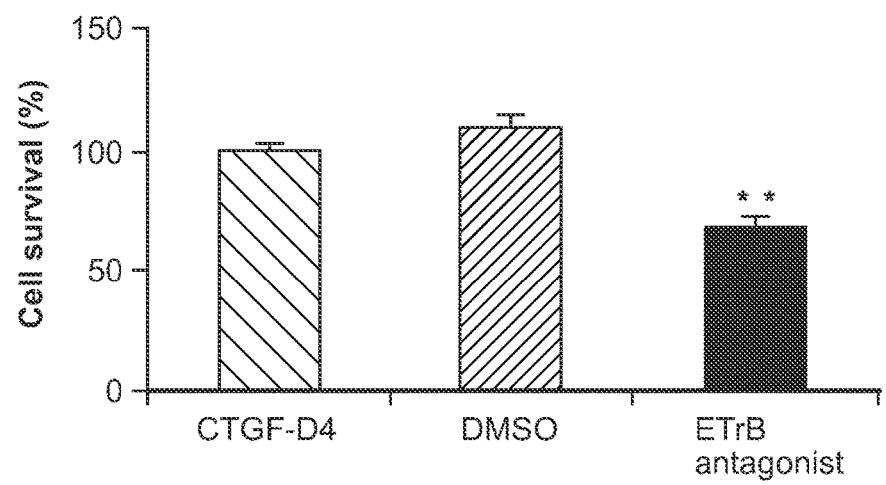
FIG. 14D is a graph depicting that a pharmacological antagonist to ETrB reduced EPDC survival under hypoxic conditions (1% oxygen, 48 hrs).
Figure 14E:
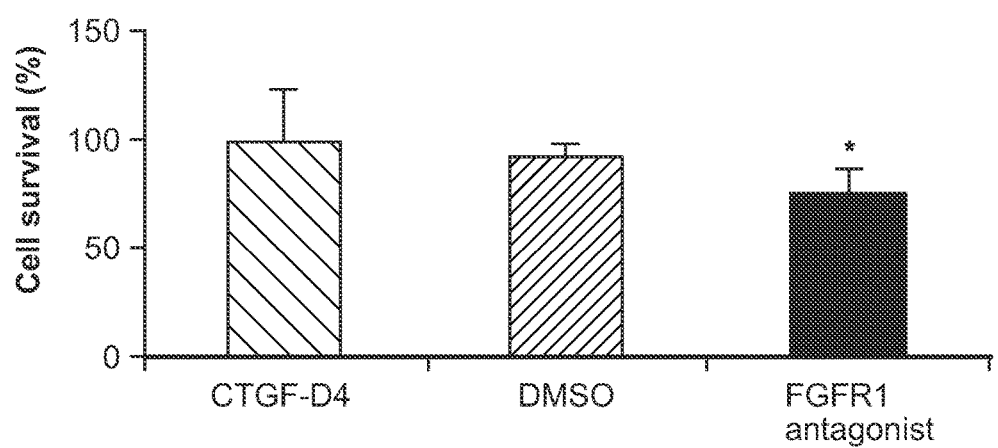
FIG. 14E is a graph depicting that a pharmacological antagonist to FGFR1 reduced EPDC survival under hypoxic conditions (1% oxygen, 48 hrs).

In ex vivo adhesion assays with EPDCs, CTGF-D4 (40 ng/ml) promoted adhesion of EPDCs to fibronectin (FIG. 14A). Exposure to CTGF-D4 also promoted EMT-like differentiation in EPDCs, increasing protein levels of smooth muscle actin (SMA), the adhesion/migration mediator Thy-1 (CD90), and the Endothelin Type B receptor (ETrB)(FIG. 14B). Levels of Von Willebrand Factor, an endothelial-specific cell marker, did not seem to be affected by CTGF-D4 (FIG. 14B). Notably, co-incubation of EPDCs in CTGF-D4 and anti-Lrp6 strongly reduced SMA, CD90, and ETrB protein levels (FIG. 14C). Furthermore, co-incubation in CTGF-D4 and anti-Lrp6 markedly increased Keratin protein expression (FIG. 14C). Without being bound to a particular theory, this may indicate a reversal of EMT back toward an epithelial (mesothelial) state. Multiple neutralizing antisera and pharmacological inhibitors were screened for a variety of cell surface receptors to interrogate their potential role in CTGF-D4 signaling in EPDCs. Drug antagonists to ETrB and FGFR1 significantly reduced cell protection conferred by CTGF-D4 under hypoxic conditions (ETrB antagonist, $p<0.01$; FGFR1 antagonist, $p<0.05$; FIGS. 14D and 14E).

Example 11

Epicardial-Derived Cell (EPDC) CdM Provided Vascular Protection In Vivo and In Vitro To examine EPDC CdM-mediated vascular protection, cardiac endothelial cell protection assays were performed under conditions of simulated ischemia: low glucose medium and 1% oxygen for 24 or 48 hrs. Compared with incubation in MEM (vehicle control), unconcentrated CdM (1× CdM) generated from EPDC protected cardiac endothelial cells from hypoxic/ischemic injury for 24 hr in this assay. CdM concentrated 10-fold (10× CdM) provided a greater level of cell protection than did 1× CdM, protecting coronary artery endothelial cells, microvascular endothelial cells and aortic endothelial cells for 48 hr.

Figure 15B:
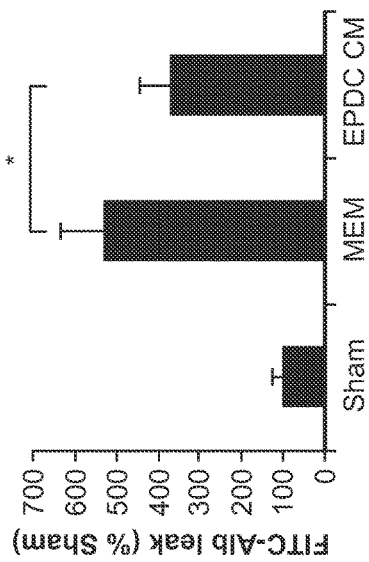
FIG. 15B is a graph showing that delivery of EPDC CdM into the left ventricle lumen (intra-arterial) reduced vascular leak after MI and reperfusion.
Figure 15A:
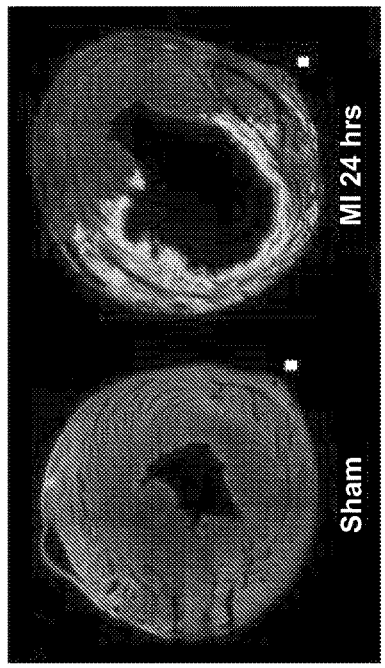
FIG. 15A are images depicting FITC-albumin extravasation in heart with MI (left panel: sham; right panel, CdM).

To determine whether EPDC CdM could provide vascular protection in vivo, adult male Fischer rats underwent 2 hr of ischemia followed by 24 hr of reperfusion. They were then treated with either MEM (vehicle control, MEM) or 30× EPDC CdM at the time of reperfusion. Two hours prior to harvesting the heart, each rat was injected with 0.5 ml of FITC-albumin (5mg/ml) through the tail vein. Hearts were then harvested and homogenized. Twenty-four hours after ischemia/reperfusion we quantified the amount of FITC extravasation in each treated animal by normalizing it to extravasation in sham-operated rats that were also injected with FITC-albumin. Heart homogenates from EPDC CdM-treated rats contained 37.8% greater FITC fluorescence that those from rats that received vehicle. The amount of extravasated FITC-albumin in the vehicle-treated group was 527.4%±109.33 of sham (n=5), while in the CdM-treated group it was 359.7724%±78.82 of sham (n=5)(FIGS. 15A and 15B). Thus, EPDC CdM contains factors that promote blood vessel integrity early after reperfusion.

Figure 15D:
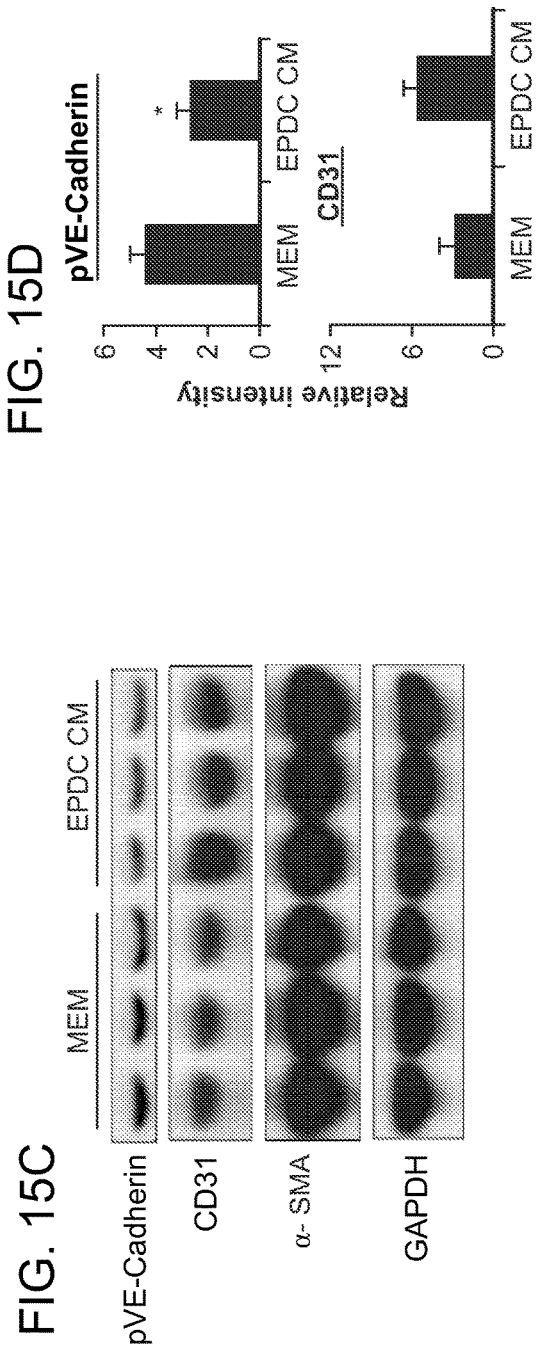
FIG. 15D are graphs depicting the relative intensity of p-VE-Cadherin (upper panel) and CD31 (bottom panel) in MEM and EPDC-CdM treated subjects. The level of p-VE-Cadherin decreased and the level of CD31 significantly increased indicating that EPDC CdM protected endothelial cells from reperfusion injury.
Figure 15C:
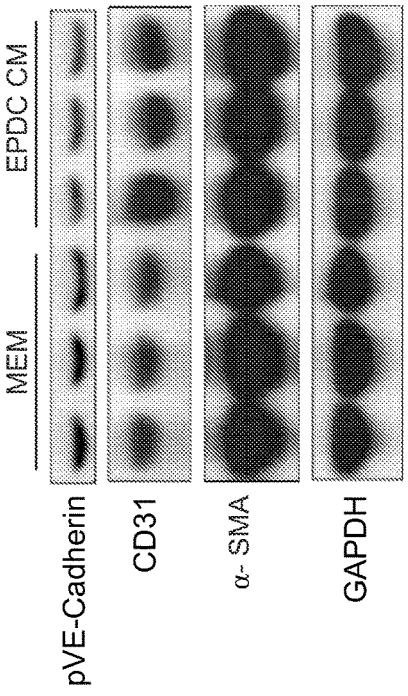
FIG. 15C are Western Blots depicting that treatment with EPDC CdM at the time of reperfusion significantly reduced the level of p-VE-Cadherin and significantly increased the levels of CD31. This indicates that EPDC CdM protected endothelial cells from reperfusion injury.

To understand the effects of EPDC CdM on blood vessels, immunoblotting was performed on the soluble fraction from left ventricle homogenates. VE-Cadherin plays a key role in maintaining endothelial barrier integrity, and the level of phosphorylated VE-Cadherin (pVE-Cadherin) is a marker for increased vascular permeability. At 1 day after MI, reperfusion, and treatment, the level of pVE-Cadherin was significantly higher in the MEM group of animals than in the EPDC CdM group ($p \leq 0.05$, n=3; FIGS. 15C and 15D). To examine the relative effects of EPDC CdM treatment on vascular endothelial cells and smooth muscle cells, the levels of CD31 (PECAM1, endothelial marker) and smooth muscle alpha actin (SMA) were compared in LV homogenates from vehicle- and EPDC CdM-treated groups. Consistent with endothelial cell survival, significantly higher levels of CD31 were observed in animals treated with EPDC CdM in comparison with vehicle controls ($p \leq 0.05$, n=3; FIGS. 15C and 15D). In contrast to the CD31 results, equal amounts of soluble SMA in vehicle- and EPDC CdM-treated animals were observed (FIG. 15C). These data indicate that EPDCs secrete a factor or factors that reduce vascular permeability and increase endothelial cell survival.

Materials and Methods

Preparation and Isolation of Human Stromal Progenitor Cells and Fibroblasts.

Human MSCs, p75MSCs and dermal fibroblasts were prepared with protocols approved by an Institutional Review Board (Bakondi et al., Mol Ther 2009; 17(11):1938-1947). To obtain MSCs, bone marrow aspirates were taken from the iliac crest of healthy adult donors. Mononuclear cells were isolated with the use of density gradient centrifugation (Ficoll-Paque, Amersham Pharmacia Biotech) and resuspended in complete culture medium consisting of Alpha-MEM (GIBCO/BRL, Grand Island, NY); 17% FBS (Atlanta Biologicals, Norcross, Ga.); 100 units/ml penicillin (GIBCO/BRL); 100 µg/ml streptomycin (GIBCO/BRL); and 2 mM L-glutamine (GIBCO/BRL). Cells were plated in 20 ml of medium in a 150 cm² culture dish and incubated in a humidified incubator (Thermo Electron, Forma Series II, Waltham, Mass.) with 95% air and 5% $CO_2$ at 37° C. After 24 hr, nonadherent cells were removed. Adherent cells were washed twice with PBS and incubated with fresh medium. The primary adherent cells were cultured and propagated.

To obtain p75MSCs, bone marrow stem/progenitor cells were isolated by MACS using antibodies against the p75LNGFR. Freshly isolated bone marrow mononuclear cells from the Ficoll gradient were resuspended in 0.4 ml of PBS containing 0.5% bovine serum albumin and 2 mM EDTA. After adding mouse anti-human p75LNGFR antibody conjugated to magnetic beads (CD271, Miltenyi Biotech, Auburn, Calif.), the sample was incubated for 30 min. at 4° C., and then applied to a magnetic column (LS Column; Miltenyi Biotech). The bound fraction was eluted with 5 ml of MACS buffer and the cells were concentrated by centrifugation at 1000×g for 8 min. After re-suspension, the entire isolate was cultured in complete culture medium.

MSC-like cells appeared as small colonies after about 1 week, and the cells were expanded.

Isolation and Culture of Adult Rat Cardiac Stem/Progenitor Cells.

Adult CSCs were isolated from the ventricles of Fischer 344 rats and labeled with retroviral vector for GFP (Bakondi et al., Mol Ther 2009; 17(11):1938-1947). CSCs were cultured as floating spheres in DMEM/F12 supplemented with bFGF (10 ng/ml), EGF (20 ng/ml), LIF (10 ng/ml) and ITS. To grow adherent CPCs, CSCs were plated at 500 cells/cm$^2$ and cultured in CSC medium supplemented with 2% FBS (CPC growth medium).

Isolation and Culture of Adult Rat Cardiac Fibroblasts.

Ventricular fibroblasts were prepared with protocols approved by an Institutional Animal Care and Use Committee. Ventricular fibroblasts were isolated from hearts of adult Sprague-Dawley rats. The hearts were minced and enzymatically-dissociated into single cell suspension. Non-myocytes were separated by discontinuous density gradient centrifugation and cultured in DMEM/F-12 supplemented with 10% FCS. Passage 2 cells were used for experiments.

Preparation of Serum Free Conditioned Medium (CdM).

Passage 4 to 8 human MSCs, p75MSCs or dermal fibroblasts were cultured to 80 to 90% confluence in 150 cm$^2$ dishes with complete culture medium (Bakondi et al., Mol Ther 2009; 17(11):1938-1947). To generate CdM, cells were washed twice with PBS and incubated with 20 mls of fresh serum-free α-MEM in standard conditions without any supplements or growth factors for 48 hrs. Medium was then collected, filtered, and stored at −80° C. For some experiments, CdM was concentrated up to 10- or 30-fold with the use of a Labscale™ TFF diafiltration system (Pellicon XL 5 kDa cut-off filters, Millipore, Bedford, Mass.).

Short-Term Priming of CSCs. CSCs were cultured as spheres in serum-free CSC growth medium. CSC spheres were trypsinized and centrifuged at 1000×g for 8 min. After re-suspension in 1× PBS, cells were passed through a 40 micron filter to isolate single CSCs (cell strainer, Fisher Scientific). Cells were counted on a hemocytometer, centrifuged again, and re-suspended in 30× p75MSC CdM or Alpha-MEM (CdM vehicle control), or CTGF-D4 (3 ng/ml)/Insulin (30 ng/ml)/1% BSA, or 1% BSA in Alpha-MEM (vehicle control for recombinant peptides). CSCs were incubated in the above conditions for 30 minutes on ice prior to sub-epicardial injection.

Myocardial Infarction Surgery and CSC Transplantation in Rats.

Fischer 488 rats (males, 7 weeks of age) were weighed, shaved, anesthetized under 4% isoflurane, and endotracheally-intubated. Rats were ventilated at a respiration rate of 65 beats per min under a peak inspiration pressure of 15 cm H$_2$O (Kent Scientific). Body temperature was maintained at 37° C. with a heating pad (Gaymar). Through a dermal incision, a blunt dissection of the fascia was performed and the intercostal muscles were separated. The heart was exposed by retraction of the pericardium to expose the LAD. The LAD was occluded with a 6-0 nylon suture and occlusion was confirmed by blanching of the anterior free wall of the LV. The animals were allowed to recover off the ventilator.

After 24 hours, rats were re-intubated, ventilated, and the chest wall was re-opened. Hearts were exposed to reveal the border zones of the infarct. For each rat, we performed 2 sub-epicardial injections of CSCs (5 ul each, one per border zone) with a 30 gauge Hamilton syringe. The needle was introduced tangentially to the wall of the LV and with the bevel facing upward. The syringe was advanced only as far as the bevel edge to access the sub-epicardial surface of the heart and so as not target the underlying myocardium of the LV. After the injections, the chest wall was closed and rats recovered for 7 days prior to euthanization.

Cell Culture in CdM and Evaluation of Cell Number.

Adult rat CPCs and cardiac fibroblasts were plated at 500 cells/cm$^2$ and cultured in their respective growth mediums. Three days after plating, the medium was removed, the wells were washed twice with PBS, and the cells were then exposed to CdM or to fresh serum-free medium (Alpha-MEM). For time course proliferation studies, CdM and serum-free medium were changed every 2 days. In signal transduction inhibitor studies, the following pharmacological inhibitors were used: AG490, inhibitor of Jak2/STAT3 pathway; Stattic, inhibitor of STAT3; LY294002, inhibitor of phosphatidylinositol 3-kinase (PI3K)/Akt pathway; and PD98059, inhibitor of extracellular signal-regulated kinase (ERK). All of the inhibitors were purchased from Calbiochem (Darmstadt, Germany) and were dissolved in dimethyl sulfoxide (DMSO). CPCs were cultured in CdM with the inhibitors or with the equivalent volume of DMSO as a control for 48 hrs. In cell protection studies, 3 days after plating, medium was replaced with either the CdM or serum-free medium and the cells were exposed to hypoxia in a specialized incubator (1% oxygen) for 48 hrs. The hypoxia incubator was a model that measured both CO$_2$ and O$_2$ (Thermo Electron, Forma Series II, model 3130). Oxygen was maintained at 1% by the injection of nitrogen gas and was monitored continuously.

Cell numbers were quantified by the fluorescent labeling of nucleic acids (CyQuant dye; Molecular Probes, Carlsbad, Calif.) and with a microplate fluorescence reader (FL$_x$800; Bio-Tek Instruments Inc., Winooski, Vt.) set to 480 nm excitation and 520 nm emission. Each experiment was repeated a minimum of 3 times.

Immunocytochemistry.

CPCs were fixed with 4% paraformaldehyde in 1× PBS. Non-specific binding was limited by 1 hour incubation in PBS containing 5% goat serum and 0.4% triton X-100. Primary antibodies were incubated overnight at 4° C. After washing 3×5 min with PBS, secondary antibody that was diluted 1:1000 (Alexa 594, Molecular Probes) was applied for 1 hr at room temperature (RT). After 3×5 min washes, slides were mounted with Vectashield containing DAPI (Vector Laboratories, Burlingame, Calif.). Epifluorescence images were taken using a Leica DM6000B microscope equipped with a CCD camera (Leica DFC350Fx) and FW4000 software. The primary antibodies for immunocytochemistry were as follows: phospho-STAT3 (Tyr705, 1:50, Cell signaling, Danvers, Mass.); α-sarcomeric actin (1:500, Sigma); α-smooth muscle actin (1:800, Sigma); and von Willebrand factor (1:100, Chemicon, Temecula, Calif.). For quantification of differentiation, cells positive for α-sarcomeric actin, α-smooth muscle actin and von Willebrand factor and total cells were counted at least in three fields per slide. The percentage of positive cells was calculated for each slide (n=3 in each group).

DNA Replication Assay.

Three days after the plating, CSCs were cultured in growth medium, CdM or serum-free medium for 24 hr, and BrdU (BD Biosciences) was added at a final concentration of 10 μM. Immunocytochemistry was carried out with BrdU antibody (Sigma) and BrdU-positive cell numbers were quantified as described herein above.

Immunoblotting.

Cells were lysed in a buffer that consisted of 0.1% sodium dodecyl sulphate (SDS) and complete protease inhibitor cocktail (Roche, Basel, Switzerland) in PBS. Protein concentration was determined by the DC protein assay (Biorad, Hercules, Calif.). Twenty μg of protein was separated by SDS-PAGE. After electrophoresis, the gels were electroblotted to polyvinylidene difluoride (PVDF) membranes. All electrophoresis and electroblotting used Novex reagents and systems (Invitrogen, Carlsbad, Calif.). The blots were blocked for 1 hr at RT in 5% nonfat dry milk in PBS with 0.1% Tween 20 (PBST), washed 3×5 min in PBST, and incubated in primary antibodies in PBST with 5% BSA overnight at 4° C. After 3×5 min washes in PBST, the blots were incubated in secondary antibody conjugated to horseradish peroxidase conjugate (1:2000, Sigma) in PBST for 1 hr at RT. Unbound secondary antibody was removed and positive bands were detected with a chemiluminescent reaction. The primary antibodies for immunoblotting were Ki67 (clone SP6, 1: 200, Abcam, Cambridge, Mass.); p-STAT3 (Tyr705, 1:1000), total STAT3 (1:1000), p-Akt (Ser 473, 1:1000)(Cell signaling); and β-actin (1:5000, Sigma).

ELISAs for IGF-1, Insulin, and CTGF.

For assay of human IGF-1, 1× p75 CdM was assayed by ELIAS using commercial ELISA reagents according to manufacturer's protocol (R and D Systems). For assay of Insulin and CTGF, high protein-binding plates were incubated with 1 or 10× p75 CdM overnight at room temperature to capture antigens from CdM. Wells were then washed with mild detergent (0.05% Tween-20 in PBS) followed by blocking with 1% BSA in PBS for 1 hour. After blocking buffer was thoroughly washed off from the wells, samples were incubated with 100 μl of biotin-conjugated polyclonal antibody to CTGF at 5 μg/100 μl (Peprotech) for 2 hours at room temperature. Polyclonal mouse anti-Insulin antibody (Santa Cruz) was incubated for 2 hours at room temperature, followed by 3 washes with wash buffer. The wells were then incubated in anti-mouse biotin conjugated IgG (Sigma Aldrich) for 2 hours at room temperature. After washing in wash buffer 3 times, samples for CTGF and Insulin ELISA were incubated in Streptavidin conjugated HRP (1:2000) for 2 hrs at room temperature, followed by washing and addition of 100 μl of substrate ABTS (Thermo Scientific; #37615) for 20 minutes. Absorbance was measured (450 nm) on a Synergy HT plate reader.

Myocardial Infarction Surgery in Mice.

Male mice at 8-10 weeks of age underwent permanent ligation of the Left Anterior Descending Coronary Artery (LAD) to induce myocardial infarction (C57b16 mice, Taconic, Hudson, N.Y.). Mice were not included in the study if they did not survive the initial MI surgery, did not achieve a successful MI (blanching observed at time of treatment), or died during treatment application. Following all procedures, mice were given analgesia (buprenorphine, 0.05-0.1 mg/kg i.p.) and monitored for signs of distress until termination of the study. All procedures were done in accordance with protocols approved by an Institutional Animal Care and Use Committee.

For permanent LAD ligation surgery, mice were anesthetized with 2-4% Isoflurane, shaved, weighed, intubated, and then maintained for the duration of the procedure on a sterile surgical field with the use of a mechanical ventilation system (MiniVent, Harvard Apparatus, Holliston, Mass.). Throughout the surgery and during the recovery period, body temperatures were maintained with a heated water pad system (Gaymar T-Pump TP-500, Gaymar Industries, Orchard Park, N.Y.). Viewing the chest through a dissecting microscope (Stemi 2000-C, Carl Zeiss MicroImaging, Thornwood, N.Y.) a dermal incision was made, the underlying fascia were removed, and the thoracic musculature was retracted to expose the left ribcage. Next the intercostal muscles were retracted and the outer (parietal or visceral) pericardium was removed to expose the LAD. The LAD was then ligated (2.0-3.0 mm from left atrial apex) with 8.0 nylon suture (Henry Schein, Melville, N.Y.) and blanching within the myocardium of the left ventricle was noted. The intercostals were rejoined with a 6.0 nylon suture (Henry Schein), the lungs were reinflated, and overlying dermis rejoined with a 6.0 nylon suture. All mice were recovered to an ambulatory state prior to any subsequent treatment procedure. Survival after the MI surgery was >90%. Sham-operated mice underwent all procedures except that the suture was placed under the LAD but was not ligated.

Infusion of p75MSC CdM After MI in Mice.

To evaluate p75 CdM treatment in an unbiased manner, all animals were randomized to treatment (after LAD ligation). Following 24 hour recovery of an animal after the first surgery, the mouse was then again anesthetized, intubated, and the chest opened. Once the intact suture and area of blanching were confirmed, 30× p75 CdM (200 μL) or vehicle (Alpha-MEM, 200 μL) warmed to 37° C. was delivered to the entire cardiovascular arterial tree by injecting the solution into the lumen of the left ventricle (LV). Injections were performed slowly (over a period of 1 minute) with a 30.5 gauge needle inserted below the great cardiac vein (LV apex) at an angle 45° to the myocardium. Following treatment with either CdM or vehicle, the needle was removed and the intercostals were rejoined using 6.0 chromic gut suture (Ethicon, Johnson and Johnson, Inc., Livingston, UK), lungs then reinflated, and overlying dermis rejoined with 6.0 nylon suture. All mice were then recovered to an ambulatory state and transferred to the vivarium for the remaining duration of the experiment.

Echocardiography.

Two dimensional, Doppler, and M-Mode echocardiography was performed with a Vevo 770 High-Resolution Imaging System (VisualSonics, Toronto, ON, Canada). Data were recorded from sham-operated mice, vehicle-treated mice with MI, and CdM-treated mice with MI while under isoflurane anesthesia. All left ventricular dimensions in systole and diastole were measured from M-mode images obtained at the mid-papillary muscle level. Echocardiographic data were coded for unbiased measurements and determination of ECHO wall motion scores. ECHO scores were determined from functional assessment of 13 segments with a model based on the Amercian Society of Echocardiography 17 segment model. Systolic wall motion scores were assigned to 4 quadrants each of 3 short axis segments taken at apical, mid papillary, and basal levels, with an additional segment at the apex (13 total). Scores were assigned as: 1=normal, >25% motion; 2=hypokinetic, 10-25% motion; 3=akinetic, <10% motion. Pulmonary arterial Doppler flow velocities and volumes were quantified (Baumann et al. Echocardiography 2008; 25:739-748).

Following ECHO, the mice were killed humanely by exsanguination and the hearts were removed and rinsed in PBS. For CK assays, left ventricular tissue was dissected away from the atria and the aorta, further separated into anterior LV and posterior LV/septum, and immediately snap frozen by submersion of cryovials in liquid N2. The LV tissues were maintained at −80° C. until the day of the CK assay (see below).

TUNEL Assay.

TUNEL was performed as reported previously (French et al. FASEB J 2009; 23:1177-1185). Quantification of TUNEL-positive cells within zones of infarction was performed in an unbiased fashion by a viewer that was blinded to slide (sample) identity. Cells were counted with Image Pro Plus Software as reported previously (French et al. FASEB J 2009; 23:1177-1185).

Creatine Kinase Assay.

The remaining creatine kinase (CK) activity in left ventricular tissues was assessed to determine the extent of infarction in mouse hearts as reported previously (Kjekshus et al. Circ Res 1970; 27:403-414; Zaman et al. Exp Biol Med. 2011; 236:598-603.). The loss of CK activity directly reflects the loss of viable myocardium after MI. The percentage of left ventricle with infarction was calculated based on observed total LV CK activity (IU/mg protein) in left ventricles of normal hearts without infarction. The percent of MI=100×[NL CK-LV CK]/Δ, where NL CK is the amount of CK in tissue from normal LV (IU/mg of soluble protein), LV CK is total remaining CK activity in the LV after MI (IU/mg soluble protein), and Δ is the difference between the amount of CK in normal zones of myocardium and in zones of myocardium with infarction.

Immunohistochemistry.

Rats were euthanized under isoflurane, their hearts harvested and washed in PBS to remove remnant blood. Hearts were fixed in 4% paraformaldehyde overnight and equilibrated in 15 and 30% sucrose consecutively for cryoprotection. After mounting in OCT (Tissue-Tek), serial sections were performed from apex to base at 20 microns (Leica CM1800 Cryostat) and sections were mounted on glass slides. Slides were dried at 37° C. and washed twice in 1× PBS. Primary antibodies were against Ki67 (clone SP6, 1:100; Abcam), CD31, (1:50, BD Biosciences), and smooth muscle alpha actin (1:500, Sigma). Primary antibodies were detected with secondary antibodies conjugated to Alexa 594 (1:2000). Slides were mounted in Vectashield with DAPI (Vector Labs). Sections were imaged by epifluoresence deconvolution microscopy (Leica DM6000B; Leica) with Leica FW4000 software.

Statistical Analysis.

Comparisons of parameters among the three groups were made with one-way analysis of variance (ANOVA) followed by Scheffé's multiple comparison test. Comparisons of parameters between two groups were made by unpaired Student's t-test. P<0.05 was considered significant.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

This application may be related to U.S. patent application Ser. No. 13/220,555, which is a continuation-in-part application of International Patent Application No.: PCT/US2010/001540, filed May 26, 2010, which claims the benefit of U.S. Provisional Application Ser. No. 61/181,071, filed May 26, 2009, the disclosures of which are hereby incorporated herein in their entireties by reference.

All patents and publications mentioned in this specification are herein incorporated by reference to the same extent as if each independent patent and publication was specifically and individually indicated to be incorporated by reference.

What is claimed is:

1. A method for enhancing engraftment of a cardiac cell or progenitor thereof, the method comprising contacting the cardiac cell or progenitor thereof with a composition comprising (a) one or more of connective tissue growth factor (CTGF) having at least 95% amino acid sequence identity to SEQ ID NO: 1 and human C-terminal CTGF peptide having at least 95% amino acid sequence identity to SEQ ID NO: 2 or 3; and (b) one or more of insulin comprising polypeptides having at least 95% amino acid sequence identity to SEQ ID NOs: 6 and 7 and IGF-1 having at least 95% amino acid sequence identity to SEQ ID NO: 8, thereby enhancing engraftment.

2. The method of claim 1, wherein the method stabilizes or reduces cardiac tissue damage in a subject.

3. The method of claim 1, wherein the cardiac cell or progenitor is contacted in vitro or in vivo.

4. The method of claim 3, wherein following contact of the cardiac cell or progenitor in vitro, the cell is administered to a subject.

5. A method for enhancing engraftment of a cardiac cell or progenitor thereof in a subject, the method comprising:
(a) contacting the cardiac cell or progenitor thereof in vitro with a composition comprising (i) one or more of connective tissue growth factor (CTGF) having at least 95% amino acid sequence identity to SEQ ID NO: 1 and human C-terminal CTGF peptide having at least 95% amino acid sequence identity to SEQ ID NO: 2 or 3; and (ii) one or more of insulin comprising polypeptides having at least 95% amino acid sequence identity to SEQ ID NOs: 6 and 7 and IGF-1 having at least 95% amino acid sequence identity to SEQ ID NO: 8, thereby generating a primed cell; and
(b) administering the primed cell to the subject, thereby enhancing engraftment of the cell in the subject.

6. The method of claim 5, wherein the cardiac cell or progenitor is autologous or heterologous.

7. The method of claim 5, wherein the cardiac cell is selected from the group consisting of an adult cardiac myocyte, adult cardiac endothelial cell, adult cardiac smooth muscle cell, adult cardiac fibroblast, adult cardiac stem cell, adult cardiac progenitor cell, adult vascular stem cell, adult epicardial cell, adult sub-epicardial cell, adult bone marrow-derived stem or progenitor cell, cardiac derivative from embryonic stem (ES) cells, and induced pluripotent stem (iPS) cell.

8. The method of claim 7, wherein the subject has a disease or disorder selected from the group consisting of myocardial infarction, congestive heart failure, stroke, and ischemia.

* * * * *